(12) United States Patent
Bowman et al.

(10) Patent No.: US 9,416,221 B2
(45) Date of Patent: Aug. 16, 2016

(54) BIODEGRADABLE TERPOLYMERS AND TERPOLYMER BLENDS AS PRESSURE-SENSITIVE ADHESIVES

(75) Inventors: Howard Bowman, Birmingham, AL (US); Don Lucast, North St. Paul, MN (US); Philip Morris, Hoover, AL (US)

(73) Assignee: SurModics, Inc., Eden Prairie, MN (US)

( * ) Notice: Subject to any disclaimer, the term of this patent is extended or adjusted under 35 U.S.C. 154(b) by 614 days.

(21) Appl. No.: 13/221,464

(22) Filed: Aug. 30, 2011

(65) Prior Publication Data

US 2012/0078155 A1    Mar. 29, 2012

Related U.S. Application Data

(60) Provisional application No. 61/378,134, filed on Aug. 30, 2010, provisional application No. 61/378,212, filed on Aug. 30, 2010, provisional application No. 61/380,937, filed on Sep. 8, 2010, provisional application No. 61/378,235, filed on Aug. 30, 2010.

(51) Int. Cl.
*C09J 7/02* (2006.01)
*A61L 15/58* (2006.01)
(Continued)

(52) U.S. Cl.
CPC .............. *C08G 63/08* (2013.01); *A61L 15/26* (2013.01); *A61L 15/58* (2013.01); *A61L 24/046* (2013.01); *C09J 7/00* (2013.01); *C09J 7/0207* (2013.01); *C09J 7/0285* (2013.01); *C09J 167/04* (2013.01); *C08L 67/04* (2013.01); *C09J 2467/00* (2013.01); *C09J 2467/006* (2013.01); *Y10T 428/1334* (2015.01); *Y10T 428/1352* (2015.01); *Y10T 428/1476* (2015.01); *Y10T 428/21* (2015.01); *Y10T 428/24777* (2015.01); *Y10T 428/24942* (2015.01); *Y10T 428/249921* (2015.04); *Y10T 428/2839* (2015.01); *Y10T 428/2865* (2015.01); *Y10T 428/31681* (2015.04); *Y10T 428/31786* (2015.04); *Y10T 428/31855* (2015.04); *Y10T 442/172* (2015.04)

(58) Field of Classification Search
None
See application file for complete search history.

(56) References Cited

U.S. PATENT DOCUMENTS

| | | | |
|---|---|---|---|
| 4,020,558 A | 5/1977 | Cournut et al. | |
| 4,241,489 A | 12/1980 | Manning | |

(Continued)

FOREIGN PATENT DOCUMENTS

| | | |
|---|---|---|
| CA | 2705520 | 5/2009 |
| EP | 0306212 | 3/1989 |

(Continued)

OTHER PUBLICATIONS

Beletsi et al. (Effect of preparative variables on the properties of poly(dl-lactide-co-glycolide)-methoxypoly(ethyleneglycol) copolymers related to their application in controlled drug delivery, Int. J. of Pharm. 182 (1999) 187-197).*

(Continued)

*Primary Examiner* — Alexandre Ferre
(74) *Attorney, Agent, or Firm* — Pauly, DeVries Smith & Deffner, L.L.C.

(57) ABSTRACT

Disclosed herein are terpolymers and blends prepared from polyester terpolymers that can function as pressure-sensitive adhesives. The disclosed articles can comprise the terpolymer and terpolymer blends coated to a conformable backing member. The terpolymer and terpolymer blends can further comprise a bioactive agent.

20 Claims, 2 Drawing Sheets

(51) Int. Cl.
  *C09J 7/04* (2006.01)
  *A61F 13/02* (2006.01)
  *B32B 7/12* (2006.01)
  *B32B 1/02* (2006.01)
  *C08G 63/08* (2006.01)
  *A61L 15/26* (2006.01)
  *A61L 24/04* (2006.01)
  *C09J 7/00* (2006.01)
  *C09J 167/04* (2006.01)
  *C08L 67/04* (2006.01)

(56) References Cited

U.S. PATENT DOCUMENTS

| | | | |
|---|---|---|---|
| 4,595,713 A | 6/1986 | St. John |
| 4,704,692 A | 11/1987 | Ladner |
| 4,804,691 A | 2/1989 | English et al. |
| 4,874,612 A | 10/1989 | Deasy |
| 4,892,736 A | 1/1990 | Goodson |
| 4,898,734 A | 2/1990 | Mathiowitz et al. |
| 5,004,602 A | 4/1991 | Hutchinson |
| 5,076,807 A | 12/1991 | Bezwada et al. |
| 5,278,201 A | 1/1994 | Dunn et al. |
| 5,281,354 A | 1/1994 | Faber |
| 5,407,609 A | 4/1995 | Tice et al. |
| 5,468,253 A | 11/1995 | Bezwada et al. |
| 5,496,605 A | 3/1996 | Augst et al. |
| 5,514,378 A | 5/1996 | Mikos et al. |
| 5,558,877 A | 9/1996 | Matlin et al. |
| 5,568,866 A | 10/1996 | Grosskopf et al. |
| 5,599,552 A | 2/1997 | Dunn et al. |
| 5,599,852 A | 2/1997 | Scopelianos et al. |
| 5,665,477 A | 9/1997 | Meathrel et al. |
| 5,702,716 A | 12/1997 | Dunn et al. |
| 5,702,717 A | 12/1997 | Cha et al. |
| 5,707,647 A | 1/1998 | Dunn et al. |
| 5,739,176 A | 4/1998 | Dunn et al. |
| 5,759,563 A | 6/1998 | Yewey et al. |
| 5,853,876 A | 12/1998 | Takano et al. |
| 5,876,452 A | 3/1999 | Athanasiou et al. |
| 5,945,115 A | 8/1999 | Dunn et al. |
| 6,006,122 A | 12/1999 | Smits |
| 6,086,526 A | 7/2000 | Francischelli |
| 6,126,919 A | 10/2000 | Stefely et al. |
| 6,130,200 A | 10/2000 | Brodbeck et al. |
| 6,149,614 A | 11/2000 | Dunshee et al. |
| 6,224,622 B1 | 5/2001 | Kotzev |
| 6,324,435 B1 | 11/2001 | Shchervinsky et al. |
| 6,331,311 B1 | 12/2001 | Brodbeck et al. |
| 6,338,859 B1 | 1/2002 | Leroux et al. |
| 6,406,745 B1 | 6/2002 | Talton |
| 6,413,536 B1 | 7/2002 | Gibson et al. |
| 6,432,438 B1 | 8/2002 | Shukla |
| 6,467,621 B1 | 10/2002 | Ishida |
| 6,468,961 B1 | 10/2002 | Brodbeck et al. |
| 6,469,132 B1 | 10/2002 | Eisenberg et al. |
| 6,471,987 B1 | 10/2002 | McBride-Sakal et al. |
| 6,477,428 B1 | 11/2002 | Skinner et al. |
| RE37,950 E | 12/2002 | Dunn et al. |
| 6,673,767 B1 | 1/2004 | Brodbeck et al. |
| 6,742,522 B1* | 6/2004 | Baker et al. ............ 128/849 |
| 6,747,121 B2 | 6/2004 | Gogolewski |
| 6,845,352 B1 | 1/2005 | Wang |
| 6,846,795 B2 | 1/2005 | Lant et al. |
| 6,849,426 B2 | 2/2005 | Chen et al. |
| 6,852,816 B2 | 2/2005 | Lewis et al. |
| 6,923,985 B2 | 8/2005 | Peterson et al. |
| 6,936,052 B2* | 8/2005 | Gellman et al. ........... 606/99 |
| 6,939,569 B1 | 9/2005 | Green et al. |
| 7,008,979 B2 | 3/2006 | Schottman et al. |
| 7,022,343 B2 | 4/2006 | Philbrook et al. |
| 7,053,209 B1 | 5/2006 | Gibson et al. |
| 7,074,426 B2 | 7/2006 | Kochinke |
| 7,122,205 B2 | 10/2006 | Peterson et al. |
| 7,128,927 B1 | 10/2006 | Dunn |
| 7,153,520 B2 | 12/2006 | Seo et al. |
| 7,299,905 B2 | 11/2007 | Yamaguchi et al. |
| 7,798,954 B2 | 9/2010 | Birk et al. |
| 8,025,635 B2 | 9/2011 | Eaton et al. |
| 8,492,512 B2 | 7/2013 | Raiche et al. |
| 8,920,921 B2 | 12/2014 | Bowman et al. |
| 8,951,546 B2 | 2/2015 | Tice |
| 8,974,808 B2 | 3/2015 | Tipton et al. |
| 9,090,737 B2 | 7/2015 | Markland et al. |
| 2001/0000142 A1 | 4/2001 | Santos et al. |
| 2002/0034533 A1 | 3/2002 | Peterson et al. |
| 2002/0150622 A1 | 10/2002 | Philbrook et al. |
| 2003/0026967 A1* | 2/2003 | Joseph et al. ............ 428/292.1 |
| 2003/0068600 A1 | 4/2003 | Ellison |
| 2003/0114637 A1 | 6/2003 | Gogolewski |
| 2003/0185872 A1 | 10/2003 | Kochinke |
| 2003/0203991 A1 | 10/2003 | Schottman et al. |
| 2004/0006199 A1 | 1/2004 | Newman, Jr. et al. |
| 2004/0037885 A1 | 2/2004 | Seo et al. |
| 2004/0052859 A1 | 3/2004 | Wu et al. |
| 2004/0116025 A1* | 6/2004 | Gogins et al. ............ 442/340 |
| 2004/0146546 A1 | 7/2004 | Gravett et al. |
| 2004/0224132 A1* | 11/2004 | Roe et al. ............ 428/175 |
| 2005/0008671 A1 | 1/2005 | Van Antwerp |
| 2005/0079202 A1* | 4/2005 | Chen et al. ............ 424/426 |
| 2005/0129732 A1 | 6/2005 | Rubsamen |
| 2005/0267543 A1 | 12/2005 | Heruth et al. |
| 2006/0039952 A1 | 2/2006 | Yaacobi et al. |
| 2006/0147491 A1 | 7/2006 | Dewitt et al. |
| 2006/0212113 A1 | 9/2006 | Shaolian et al. |
| 2007/0005094 A1 | 1/2007 | Eaton et al. |
| 2007/0190154 A1 | 8/2007 | Zeigerson |
| 2007/0202145 A1 | 8/2007 | Ghabrial et al. |
| 2007/0207189 A1 | 9/2007 | Belcheva et al. |
| 2007/0231365 A1 | 10/2007 | Wang et al. |
| 2007/0265645 A1 | 11/2007 | Birk et al. |
| 2008/0051868 A1 | 2/2008 | Cottone et al. |
| 2008/0118541 A1 | 5/2008 | Pacetti |
| 2008/0125728 A1 | 5/2008 | Bischoff et al. |
| 2008/0128315 A1 | 6/2008 | Buevich et al. |
| 2008/0208323 A1 | 8/2008 | El-kurdi et al. |
| 2008/0260796 A1 | 10/2008 | Bischoff et al. |
| 2009/0004243 A1 | 1/2009 | Pacetti et al. |
| 2009/0124535 A1* | 5/2009 | Markland et al. ............ 514/2 |
| 2009/0198197 A1 | 8/2009 | Bischoff et al. |
| 2010/0098744 A1 | 4/2010 | Ferris et al. |
| 2010/0158969 A1 | 6/2010 | Tice |
| 2010/0158970 A1 | 6/2010 | Tipton et al. |
| 2010/0158978 A1 | 6/2010 | Markland |
| 2010/0160891 A1 | 6/2010 | Tipton et al. |
| 2010/0160892 A1 | 6/2010 | Tice |
| 2010/0168807 A1 | 7/2010 | Burton et al. |
| 2010/0198278 A1 | 8/2010 | Cobian et al. |
| 2010/0203100 A1 | 8/2010 | Cobian et al. |
| 2010/0247596 A1 | 9/2010 | Bischoff |
| 2011/0098813 A1 | 4/2011 | Gibson |
| 2011/0129422 A1 | 6/2011 | Markland et al. |
| 2011/0159072 A1 | 6/2011 | Missling et al. |
| 2012/0077028 A1 | 3/2012 | Bowman et al. |
| 2012/0077887 A1 | 3/2012 | Bowman et al. |
| 2012/0077954 A1 | 3/2012 | Raiche et al. |
| 2016/0082110 A1 | 3/2016 | Burton et al. |

FOREIGN PATENT DOCUMENTS

| | | |
|---|---|---|
| EP | 1375557 | 2/2004 |
| EP | 1917971 | 5/2008 |
| EP | 2050474 | 4/2009 |
| EP | 2123312 | 11/2009 |
| EP | 2219620 | 8/2010 |
| EP | 2611868 | 7/2013 |
| JP | 08206191 | 8/1996 |
| JP | 11181077 | 7/1999 |
| JP | 11343228 | 12/1999 |
| JP | 2000159865 | 6/2000 |
| JP | 2001335623 | 12/2001 |
| WO | 9738676 | 10/1997 |
| WO | 0245689 | 6/2002 |

(56) References Cited

FOREIGN PATENT DOCUMENTS

| WO | 2006124021 | 11/2006 |
|---|---|---|
| WO | 2009064442 | 5/2009 |
| WO | 2010075298 | 7/2010 |
| WO | 2012030819 | 3/2012 |
| WO | 2012030821 | 3/2012 |
| WO | 2012030822 | 3/2012 |
| WO | 2012030823 | 3/2012 |

OTHER PUBLICATIONS

Bodansky, M. et al., "Utilization of Poly Glycerol Esters", Ed. Principles of Peptide Synthesis, Springer-Verlag, Inc, N.Y., 1993, (p. 1938-1942).
Final Office Action, for U.S. Appl. No. 12/644,097, mailed Feb. 28, 2013 (28 pages).
Final Office Action, for Japanese Patent Application No. 2010-534036, mailed Nov. 6, 2013 (4 pages) with English translation.
Final Office Action, for U.S. Appl. No. 12/269,135, mailed Mar. 21, 2014 (29 pages).
Final Office Action, for U.S. Appl. No. 12/644,097, mailed Apr. 9, 2014 (20 pages).
Final Office Action, for U.S. Appl. No. 13/221,389, mailed Sep. 10, 2013 (38 pages).
Final Office Action, from U.S. Appl. No. 12/643,558, mailed May 10, 2013, 15 pages.
"Final Office Action", mailed Apr. 9, 2012 in co pending U.S. Appl. No. 12/644,097, "Bioactive Terpolymer Compositions and Methods of Making and Using Same," (16 pages).
"Final Office Action", mailed Dec. 2, 2011 in co pending U.S. Appl. No. 12/643,558, "Flexible Implantable Composites and Implants Comprising Same," (19 Pages).
"Final Office Action", mailed Jun. 3, 2011 in co pending U.S. Appl. No. 12/269,135, "Viscous Terpolymers as Drug Delivery Platform," (24 pages).
"Final Office Action", mailed May 18, 2012 in U.S. Appl. No. 12/643,546, "Elastic Implantable Composites and Implants Comprising Same," (11 pages).
"Final Office Action", mailed Oct. 28, 2011 in co-pending U.S. Appl. No. 12/643,571, "Implantable Suction Cup Composites and Implants Comprising Same," (22 pages).
"Final Office Action", mailed Sep. 27, 2012 in U.S. Appl. No. 12/643,580, "Bioactive Spray Coating Compositions and Methods of Making and Uses Thereof," (8 pages).
Gollwitzer, et al., "Antibacterial poly(D,L-lactic acid) coating of medical implants using a biodegradable drug delivery technology", Journal of Antimicrobial Chemotherapy, 2003, pp. 585-591.
Grant,, "Synthetic Peptides: A User Guide", W.H. Freemean and Co., N.Y., 1992, (25 pgs).
Harlow, Ed, "Antibodies, a Laboratory Manual", Cold Spring Harbor Publications, N.Y., 1988, (4 pages).
Hong, et al., "Generating Elastic, Biodegradable Poolyurethane/Poly(lactide-co-glycolide) Fibrous Sheets with Controlled Antibiotic Release via Two-Stream Electrospinning", Biomacromolecules, 9, 2008, pp. 1200-1207.
"International Preliminary Report on Patentability", from International Application No. PCT/US2008/012755, mailed May 18, 2010, (5 pages).
"International Preliminary Report on Patentability", from PCT Application No. PCT/US2011/049730, mailed Mar. 14, 2013, 8 pages.
International Preliminary Report on Patentability, from PCT Application No. PCT/US2011/049731, mailed Mar. 14, 2013, 6 pages.
International Preliminary Report on Patentability, from PCT Application No. PCT/US2011/049735, mailed Mar. 14, 2013, 10 pages.
International Preliminary Report on Patentability, from PCT/US2011/049726, mailed Mar. 14, 2013, 8 pages.
"International Search Report and Written Opinion", from International Application No. PCT/US2008/012755, mailed Jan. 29, 2009, (6 pages).
"International Search Report and Written Opinion", from International Application No. PCT/US2009/069024, mailed Nov. 26, 2010, (16 pages).
"International Search Report and Written Opinion", from International Application No. PCT/US2011/049726, mailed Nov. 18, 2011, pp. 1-11.
"International Search Report and Written Opinion", from International Application No. PCT/US2011/049730, mailed Nov. 18, 2011, pp. 1-20.
"International Search Report and Written Opinion", from International Application No. PCT/US2011/049731, mailed Feb. 14, 2012, pp. 1-9.
"International Search Report and Written Opinion", from International Application No. PCT/US2011/049735, mailed Nov. 18, 2011, pp. 1-15.
Kastin, Abba J., "Handbook of Biologically Active Peptides", Academic Press, 2006, (6 pages).
Kobayashi, et al., "Bioconjugate Chem", vol. 12, pp. 100-107, (2001).
Kobayashi, et al., "Mag Res in Medicine", vol. 46, pp. 579-585, (2001).
Kulkarni, et al., "Poly(lactic acid) for Surgical Implants", Technical Rep. 6608, Walter Reed Army Medical Center, Washington, D.C., 1966.
Letsinger, et al., "Proceedings of the Naitonal Academy of Sciences", vol. 86, pp. 6553-6556, 1989.
Miller, et al., "Degradation Rates of Oral Resorbable Implants (polylactates and polyglycolates): Rate Modification iwth Changes in PLA/PGA Copolymer Ratios", J. Biomed. Matr. Res. 11, 1977, pp. 711-719, (12 pages).
Mundargi, Raghavendra C. et al., "Development and Evaluation of Novel Biodegradable Microspheres Based on poly(D,L-Lactide-co-glycolide) and poly(e-caprolactone) for Controlled Delivery of Doxycyline in the Treatment of Human Periodontal Pocket: In Vitro and In Vivo Studies", Journal of Controlled Release, vol. 119, 2007, pp. 59-68.
Nagy, et al., "Immunomodulation by tamoxifen and pergolide", Immunopharmacology, 12(2), Oct. 1986, pp. 1-2 (abstract only, pp. 1,2).
Nielson, Peter E. et al., "Bioconjug. Chem.", vol. 5, pp. 3-7, 1994.
"Non-Final Office Action", mailed Aug. 3, 2011 in co-pending U.S. Appl. No. 12/643,558, "Flexible Implantable Composites and Implants Comprising Same," (27 pages).
"Non-Final Office Action", mailed Mar. 16, 2012 in co-pending U.S. Appl. No. 12/643,580, "Bioactive Spray Coating Compositions and Methods of Making and Uses Thereof," (31 Pages).
"Non-Final Office Action", mailed Oct. 11, 2011 in co-pending U.S. Appl. No. 12/644,097, "Bioactive Terpolymer Compositions and Methods of Making and Using Same" (48 pages).
"Non-Final Office Action", for U.S. Appl. No. 12/269,135, mailed Sep. 23, 2013 (32 pages).
"Non-Final Office Action", for U.S. Appl. No. 12/643,580, mailed May 20, 2014 (10 pages).
"Non-Final Office Action", for U.S. Appl. No. 12/644,097, mailed Jul. 19, 2013 (37 pages).
"Non-Final Office Action", for U.S. Appl. No. 12/643,558, mailed Apr. 1, 2014 (26 pages).
"Non-Final Office Action", for U.S. Appl. No. 12/643,571, mailed Jul. 3, 2014 (19 pages).
"Non-Final Office Action", for U.S. Appl. No. 13/022,720, mailed Jul. 14, 2014 (35 pages).
"Non-Final Office Action", for U.S. Appl. No. 13/221,415, mailed Feb. 6, 2014 (16 pages).
"Non-Final Office Action", from U.S. Appl. No. 12/643,546, mailed Jun. 19, 2013, 12 pages.
"Non-Final Office Action", from U.S. Appl. No. 13/221,389, mailed Apr. 9, 2013, 17 pages.
"Non-Final Office Action", mailed Jan. 7, 2013 in co-pending U.S. Appl. No. 12/643,558, "Flexible Implantable Composites and Implants Comprising Same," (15 pages)., 15.
"Non-Final Office Action", mailed Dec. 15, 2011 in co-pending U.S. Appl. No. 12/643,546, 32 pages.

(56) References Cited

OTHER PUBLICATIONS

"Non-Final Office Action", mailed Jul. 5, 2012 in co-pending U.S. Appl. No. 13/221,429, "Process for Reducing Moisture in a Biodegradable Implant Device" (6 pages).
"Non-Final Office Action", mailed Jun. 8, 2011, in co-pending U.S. Appl. No. 12/643,571, (11 pages).
"Non-Final Office Action", mailed Oct. 8, 2010 in U.S. Appl. No. 12/269,135, "Viscous Terpolymers As a Drug Delivery Platform," (22 pages).
"Non-Final Office Action", mailed Sep. 20, 2012 in U.S. Appl. No. 12/644,097, "Bioactive Terpolymer Compositions and Methods of Making and Using Same," (38 pages).
"Notice of Allowance", for U.S. Appl. No. 12/643,546, mailed Feb. 21, 2014 (8 pages).
"Notice of Allowance", for U.S. Appl. No. 12/643,546, mailed Jun. 11, 2014 (14 pages).
"Notice of Allowance", for U.S. Appl. No. 13/221,415, mailed Aug. 1, 2014 (20 pages).
"Notice of Allowance", from U.S. Appl. No. 13/221,429, mailed Mar. 22, 2013, 20 pgs.
Notice of Allowance, mailed Oct. 23, 2012 in U.S. Appl. No. 13/221,429, "Process for Reducing Moisture in a Biodegradable Implant Device," (5 pages).
Office Action, from JP Application No. 2010-534036, mailed Jun. 11, 2013, 7 pages.
Plastic, The Free Dictionary, 2014 (5 pages).
Remington "The Science and Practice of Pharmacy", 21st Ed., Lippincott Williams & Wilkins, Philadelphia, PA, 2005, (14 pages).
"Response to Final Office Action", for U.S. Appl. No. 12/269,135, mailed Mar. 21, 2014 and filed with the USPTO Jun. 19, 2014 (9 pages).
"Response to Final Office Action", for U.S. Appl. No. 12/643,558, mailed May 10, 2013 and filed with the USPTO Aug. 2, 2013 (7 pages).
"Response to Final Office Action", for U.S. Appl. No. 13/221,389, mailed Sep. 10, 2013 and filed with the USPTO Jan. 10, 2014 (9 pages).
"Response to Final Office Action", Mailed Apr. 9, 2014 in co-pending U.S. Appl. No. 12/644,097, filed with the USPTO Jul. 9, 2014 (10 pages).
"Response to Final Office Action", mailed Aug. 20, 2012 in co-pending U.S. Appl. No. 12/643,546 9 pages.
"Response to Final Office Action", mailed Dec. 27, 2012 in U.S. Appl. No. 12/643,580, "Bioactive Spray Coating Compositions and Methods of Making and Uses Thereof", 5 pages.
"Response to Final Office Action", mailed Feb. 28, 2013, in co-pending U.S. Appl. No. 12/644,097, filed with USPTO May 24, 2013, (12 pages).
"Response to Final Office Action", mailed Jan. 26, 2012 in co-pending U.S. Appl. No. 12/643,571 11 pages.
"Response to Final Office Action", mailed Jul. 9, 2012 in U.S. Appl. No. 12/644,097, "Bioactive Terpolymer Compositions and Methods of Making an Dusing Same", (10 pages).
"Response to Final Office Action", mailed Mar. 2, 2012 in co-pending U.S. Appl. No. 12/643,558 10 pages.
"Response to Final Office Action", mailed Sep. 6, 2011 in U.S. Appl. No. 12/269,135, "Viscous Terpolymers As Drug Delivery Platform", 10 pages.
"Response to Non Final Office Action", mailed Jan. 3, 2012 in U.S. Appl. No. 12/644,097, "Bioactive Terpolymer Compositions and Methods of Making and Using Same", (8 pages).
"Response to Non Final Office Action", mailed Oct. 31, 2011 in U.S. Appl. No. 12/643,558, "Flexible Implantable Composites and Implants Comprising Same", (8 pages).
"Response to Non-Final Office Action", for U.S. Appl. No. 12/269,135, mailed Jan. 23, 2014 (10 pages).
"Response to Non-Final Office Action", for U.S. Appl. No. 12/643,546, mailed Jun. 19, 2013 and filed with the USPTO Dec. 19, 2013 (7 pages).
"Response to Non-Final Office Action", for U.S. Appl. No. 12/643,558, mailed Apr. 1, 2014 and filed with the USPTO Jul. 1, 2014 (7 pages).
"Response to Non-Final Office Action", for U.S. Appl. No. 12/644,097, mailed Jul. 19, 2013 and filed with the USPTO Dec. 19, 2013 (7 pages).
"Response to Non-Final Office Action", for U.S. Appl. No. 13/221,415, mailed Feb. 6, 2014 and filed with the USPTO May 6, 2014 (13 pages).
"Response to Non-Final Office Action", mailed Apr. 9, 2013, in co-pending U.S. Appl. No. 13/221,389, filed with USPTO Jul. 2, 2013 (9 pages).
"Response to Non-Final Office Action", mailed Jan. 7, 2013, in co-pending U.S. Appl. No. 12/643,558, filed with USPTO Apr. 8, 2013, (9 pages).
"Response to Non-Final Office Action", mailed Jun. 14, 2012 in co-pending U.S. Appl. No. 12/643,580 6 pages.
"Response to Non-Final Office Action", mailed Jun. 8, 2011, in co-pending U.S. Appl. No. 12/643,571, filed with USPTO Aug. 17, 2011, (10 pages).
"Response to Non-Final Office Action", mailed Mar. 14, 2012 in co-pending U.S. Appl. No. 12/643,546 8 pages.
"Response to Non-Final Office Action", mailed Oct. 2, 2012 in co-pending U.S. Appl. No. 13/221,429 5 pages.
"Response to Non-Final Office Action", mailed Oct. 8, 2010 in U.S. Appl. No. 12/269,135, filed with USPTO Apr. 8, 2011, (7 pages).
"Response to Non-Final Office Action", mailed Sep. 20, 2012, in co-pending U.S. Appl. No. 12/644,097, filed with USPTO Jan. 18, 2013, (10 pages).
Sakkas, P, "The Future: Towards Long Acting Atypical Anti-Psychosis", Annals of General Hospital Psychiatry, Oral Presentation, Dec. 23, 2003, 1 pg.
Sawhney,, "Rapidly degraded terpolymers of dl-lactide, glycolide, and [epsilon]—caprolactone with increased hydrophilicity by copolymerization with ployethers", Journal of Biomedical Materials Research, Wiley, New York, NY, US vol. 24, No. 10, Oct. 1, 1990, pp. 1397-1411.
SRISA-ARD, Mangkorn et al., "Synthesis and characterization of a random terpolymer of L-lactide, e-caprolactone and glycolide", Society of Chemical Industry, Polymer International, vol. 50, Issue 8 (Jul. 20, 2001) pp. 891-896.
Stolnik, et al., "Polylactide-Poly(ethylene glycol) micellar-like Particles as Potential Drug Carriers: Production, Colloidal Properties and Biological Performance", J. Drug Targeting, 2001 (18 pages).
Non-Final Office Action, for U.S. Appl. No. 13/221,389, mailed Aug. 25, 2014 (22 pages).
"Notice of Allowance", for U.S. Appl. No. 12/643,558, mailed Sep. 2, 2014 (14 pages).
"Final Office Action," for U.S. Appl. No. 12/643,580, mailed Mar. 23, 2015 (24 pages).
"Final Office Action," for U.S. Appl. No. 12/644,097, mailed Jun. 11, 2015 (18 pages).
"Final Office Action," for U.S. Appl. No. 13/221,389, mailed Mar. 20, 2015 (32 pages).
"Non-Final Office Action," for Japanese Patent Application No. 2013-527191, mailed May 26, 2015 (14 pages) with English Translation.
"Notice of Allowance," for U.S. Appl. No. 12/269,135, mailed Mar. 27, 2015 (28 pages).
"Response to Communication Pursuant to Rules 70(2) and 70a(2) EPC," for European Patent Application No. 08850639.9, filed on Jun. 13, 2015 (3 pages).
"Viscous," Merriam-Webster Dictionary (http:www.merriam-webster.com/dictionary/viscous) 2015 (4 pages).
US 8,920,921, 12/2014, Bowman et al. (withdrawn).
"Communication Pursuant to Rules 70(2) and 70a(2) EPC," for European Patent Application No. 08850639.9, mailed Dec. 5, 2014 (1 page).
"Extended European Search Report," for European Patent Application No. 08850639.9, mailed Nov. 19, 2014 (5 pages).
"Final Office Action," for U.S. Appl. No. 12/643,571, mailed on Jan. 5, 2015 (32 pages).

(56) References Cited

OTHER PUBLICATIONS

Lu, Chengfei et al., "Synthesis and Aggregation Behavior of four types of different Shaped PCL-PEG Block Copolymers," Polymer International, vol. 55, 2006, pp. 694-700.
"Non-Final Office Action," for U.S. Appl. No. 12/644,097, mailed Sep. 11, 2014 (26 pages).
"Notice of Allowance," for U.S. Appl. No. 12/643,546, mailed Oct. 1, 2014 (7 pages).
"Office Action," for Canadian Patent Application No. 2,705,520, mailed Jan. 20, 2015 (4 pages).
"Response Non-Final Office Action," for U.S. Appl. No. 12/644,097, mailed Sep. 11, 2014 and filed with the USPTO Feb. 11, 2015 (10 pages).
"Response to Non-Final Office Action," for U.S. Appl. No. 12/643,571, mailed Jul. 3, 2014 and filed with the USPTO Oct. 3, 2014 (10 pages).
"Response to Non-Final Office Action," for U.S. Appl. No. 12/643,580, mailed May 20, 2014 and filed with the USPTO Nov. 20, 2014 (7 pages).
"Communication Pursuant to Rules 161(1) and 162 EPC," for European Patent Application No. 11757461.6, mailed Apr. 8, 2013 (2 pages).
"Methoxy Polyethylene Glycols Technical Data Sheet," INEOS http://www.ineos.com/Show-Document/?Grade-Methoxy%20Polyethylene%20Glycol%20350&BU-INEOS%20Oxide&DocumentType-Technical%20Data%20Sheet, 2004 (4 pages).
"Non-Final Office Action," for U.S. Appl. No. 12/643,580 mailed Sep. 9, 2015 (13 pages).
"Response to Communication Pursuant to Rules 161(1) and 162 EPC," for European Patent Application No. 11757461.6, mailed Apr. 8, 2013 and filed with the EPO Aug. 6, 2013 (9 pages).
"Response to Final Office Action," for U.S. Appl. No. 12/643,580, mailed Mar. 23, 2015 and filed with the USPTO Jul. 22, 2015 (8 pages).
"Response to Office Action," for Canadian Patent Application No. 2,705,520, mailed Jan. 20, 2015 and filed with CIPO Jul. 20, 2015 (22 pages).
"Communication Pursuant to Article 94(3) EPC," for European Patent Application No. 08850639.9, mailed Nov. 24, 2015 (3 pages).
"Final Office Action," for U.S. Appl. No. 12/644,097, mailed Mar. 22, 2016 (15 pages).
"Non-Final Office Action," for Japanese Patent Application No. 2013-527191, mailed Dec. 16, 2015 (6 pages) with translation.
"Non-Final Office Action," for U.S. Appl. No. 12/643,571 mailed Nov. 18, 2015 (35 pages).
"Non-Final Office Action," for U.S. Appl. No. 13/221,389, mailed Mar. 29, 2016 (27 pages).
"Non-Final Office Action," for U.S. Appl. No. 14/955,528, mailed Mar. 11, 2016 (34 pages).
"Notice of Allowance," for Canadian Patent Application No. 2,705,520, mailed Oct. 26, 2015 (1 page).
"Notice of Allowance," for U.S. Appl. No. 12/643,571, mailed May 5, 2016 (12 pages).
"Response to Non-Final Office Action," for U.S. Appl. No. 12/643,571, mailed Nov. 18, 2015 and filed with the USPTO Feb. 18, 2016 (12 pages).

* cited by examiner

BIODEGRADABLE TERPOLYMERS AND TERPOLYMER BLENDS AS PRESSURE-SENSITIVE ADHESIVES

This application claims priority to U.S. Provisional Application No. 61/378,134, filed Aug. 30, 2010, U.S. Provisional Application No. 61/378,212, filed Aug. 30, 2010, U.S. Provisional Application No. 61/378,235, filed Aug. 30, 2010, and U.S. Provisional Application No. 61/380,937, filed Sep. 8, 2010, the content of all of which is herein incorporated by reference in its entirety.

BACKGROUND

A pressure-sensitive adhesive (PSA) can be a viscoelastic (viscous and elastic) substance capable of forming a bond with an adherent upon the application of pressure. A PSA can be soft enough to flow, or wet, but hard enough to resist flow when stress is applied. Pressure-sensitive adhesives can provide advantages over other adhesives inasmuch as they do not require cure time and other processing steps often required with the use of other adhesives.

Commercially available PSAs often include polymers such as natural rubber, polynitrile, acrylic, isobutylene, silicone and styrene. Typically, these PSAs are made from petroleum sources, have attractive fiber and structural properties, are low in cost and are easily processed. One disadvantage with many PSAs, however, is that they fail to degrade into components that can be metabolized by microbial populations or in vivo. Such PSAs are thus limited in their use in biomedical applications and other applications for which a biocompatible or biodegradable PSA would be useful.

SUMMARY

The disclosed poly(D,L-lactide-co-glycolide-co-ϵ-caprolactone) has a molecular weight of 140,000 Daltons or less and a polydispersity index (PDI) of less than 2.0. The poly(D,L-lactide-co-glycolide-co-ϵ-caprolactone) exhibits storage modulus (G') values of from about $1.5 \times 10^5$ Pa to about $5.5 \times 10^5$ Pa, over a frequency of from about 0.1 to about 1 Hz; and about $1.0 \times 10^6$ Pa to about $4.0 \times 10^6$ Pa, over a frequency of from about $10^2$ to about $10^4$ Hz at 30° C.

The disclosed article comprises a pressure-sensitive adhesive (PSA) having a first adhesive surface and an opposing second adhesive surface, the pressure-sensitive adhesive (PSA) comprising the disclosed poly(D,L-lactide-co-glycolide-co-ϵ-caprolactone); and a release liner having a surface thereof adhered to the first adhesive surface of the pressure-sensitive adhesive.

In one aspect, the blend described herein comprises: (a) a first poly(D,L-lactide-co-glycolide-co-ϵ-caprolactone) having a molecular weight ($M_w$) of from 75,000 to 250,000 Daltons and a polydispersity index (PDI) of less than 2.0, and (b) a second poly(D,L-lactide-co-glycolide-co-ϵ-caprolactone) having a molecular weight ($M_w$) of 130,000 Daltons or less and a polydispersity index (PDI) of less than 2.0; wherein the second poly(D,L-lactide-co-glycolide-co-ϵ-caprolactone) has a molecular weight ($M_w$) that is less than the first poly(D,L-lactide-co-glycolide-co-ϵ-caprolactone); and wherein the weight ratio of the first poly(D,L-lactide-co-glycolide-co-ϵ-caprolactone) to the second poly(D,L-lactide-co-glycolide-co-ϵ-caprolactone) is from about 90:10 to about 60:40.

In another aspect, the blend comprises: (a) a poly(D,L-lactide-co-glycolide-co-ϵ-caprolactone) having a molecular weight of from 75,000 to 250,000 Daltons and a polydispersity index (PDI) of less than 2.0, and (b) a poly(D,L-lactide-co-glycolide-co-mPEG) having a molecular weight ($M_w$) of less than 25,000 Daltons and a polydispersity index (PDI) of less than 2.0; wherein the poly(D,L-lactide-co-glycolide-co-mPEG) has a molecular weight ($M_w$) that is less than the poly(D,L-lactide-co-glycolide-co-ϵ-caprolactone); and wherein the weight ratio of the poly(D,L-lactide-co-glycolide-co-ϵ-caprolactone) to the poly(D,L-lactide-co-glycolide-co-mPEG) is from about 95:5 to about 75:25.

The disclosed article comprises a pressure-sensitive adhesive (PSA), the pressure-sensitive adhesive (PSA) comprising any of disclosed poly(D,L-lactide-co-glycolide-co-ϵ-caprolactone)s or blends coated to the surface of a conformable backing member, wherein the PSA coats 0.1% to 100% of the surface area of the conformable backing member. The PSA can contain a bioactive agent.

In another aspect, the pressure-sensitive adhesive (PSA) comprising any of disclosed poly(D,L-lactide-co-glycolide-co-ϵ-caprolactone)s or blends is biocompatible and biodegradable.

The disclosed article comprises a substrate having a disclosed PSA coating a surface thereof.

DETAILED DESCRIPTION

Figure 1:
FIG. 1 is a schematic illustration of an article comprising conformable backing member coated with a pressure-sensitive adhesive adhered to a release liner.

In this specification and in the claims that follow, reference will be made to a number of terms that have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

Singular forms "a," "an" and "the" include plural referents unless the context clearly dictates otherwise. Thus, for example, reference to "a bioactive agent" includes mixtures of two or more such agents, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

"Biodegradable" refers to materials that will erode to soluble species or that will degrade under physiologic conditions to smaller units or chemical species that are, themselves, non-toxic (biocompatible) to the subject and capable of being metabolized, eliminated, or excreted by the subject.

"Coating" refers to its broad definition and includes infusing, dipping, coating, adhering, impregnating, infusing or any other mode of associating a substance with a surface of material, including, but not limited to a substrate, sheet, fiber, backing or conformable backing member. As used herein, the term "coating" is intended to refer to both a layer exclusively on the surface of a material as well as a layer which can to some degree penetrate the material. In some uses described below, the "coating" can completely penetrate the material beneath the surface.

"Conformable backing member" refers to material that is conformable to a surface, including, but not limited to, anatomical surfaces. As such, when the backing is applied to a surface, it conforms to the surface. In some applications, the material is chosen conforms even when the surface is moved and stretches to accommodate the movement, but is resilient enough to continue to conform to the surface when the surface is returned to its unmoved condition. Suitable materials include, for example, nonwoven fibrous webs, woven fibrous webs, knits, films, sheets, tapes, and other familiar backing materials. Such materials can be fabricated from both natural and man-made materials, including polymeric materials.

"Glass transition temperature" or "$T_g$" refers to the glass transition temperature as determined by differential scanning calorimetry (DSC). DSC defines the glass transition as a change in the heat capacity as the polymer goes from the glass state to the rubber state. This is a second order endothermic transition (requires heat to go through the transition), and thus the transition appears as a step transition, rather than a peak as would be expected with a melting transition.

"Mole ratio," "molar ratio," and "mole percent," as used herein refer to the molar percentages of each monomer in the terpolymer. Molar percentages can be determined by $^1$H NMR analysis of the terpolymer.

"Molecular weight" or "$M_w$," as used herein, refers to the weight average molecular weight as determined by gel-permeation chromatography.

"mPEG" refers to methoxypoly(ethylene glycol).

"Optional" or "optionally" means that the subsequently described event or circumstance can or cannot occur, and that the description includes instances where the event or circumstance occurs and instances where it does not.

"Polydispersity index," or "PDI," as used herein, refers to the value obtained by dividing $M_w$ by $M_n$ (number average molecular weight). Both $M_w$ and $M_n$ are determined by gel-permeation chromatography.

Pressure-Sensitive Adhesive

The pressure-sensitive adhesive ("PSA") comprises either a single-component poly(D,L-lactide-co-glycolide-co-ε-caprolactone) adhesive or a terpolymer blend comprising poly (D,L-lactide-co-glycolide-co-ε-caprolactone) together with another poly(D,L-lactide-co-glycolide-co-ε-caprolactone) or together with a poly(D,L-lactide-co-glycolide-co-m PEG). The uses described below can comprise or consist of any the terpolymers described below. In another aspect, pressure-sensitive adhesive (PSA) comprising any of disclosed poly (D,L-lactide-co-glycolide-co-ε-caprolactone)s or blends is biocompatible and biodegradable.

(i) Single-Component PSA

The PSA comprising poly(D,L-lactide-co-glycolide-co-ε-caprolactone) can have a molecular weight ($M_w$) of 140,000 Daltons or less and a polydispersity index (PDI) of less than 2.0. The poly(D,L-lactide-co-glycolide-co-ε-caprolactone) can in some aspects exhibit storage modulus (G') values of from about $1.5 \times 10^5$ Pa to about $5.5 \times 10^5$ Pa, over a frequency of from about 0.1 to about 1 Hz; and about $1.0 \times 10^6$ Pa to about $4.0 \times 10^6$ Pa, over a frequency of from about $10^2$ to about $10^4$ Hz at 30° C.

Rheology measurements for the polymer can be determined as follows. Dynamic shear moduli determination is performed with a parallel plate rheometer (TA Instruments AR2000) at frequencies between 0.10 and 100 Hz. Oscillatory frequency sweeps are conducted at isothermal temperatures ranging from 0 to 60° C. by stepping every 10° C. for each frequency sweep. The parallel disks were 20 mm in diameter. A master curve was obtained using a temperature-dependent shift factor (WLF) with 30° C. serving as the reference temperature.

The poly(D,L-lactide-co-glycolide-co-ε-caprolactone) can be elastomeric or viscoelastic, while also exhibiting tackiness or stickiness. The terpolymer can thus function as a pressure-sensitive adhesive, which can adhere to a variety of substrates with the application of light pressure.

The poly(D,L-lactide-co-glycolide-co-ε-caprolactone) can have a molecular weight of 140,000 Daltons or less, for example from 60,000 to 140,000 Daltons, or from 60,000 to 130,000 Daltons. For example, the poly(D,L-lactide-co-glycolide-co-ε-caprolactone) can have a molecular weight ($M_w$) of 60,000, 70,000, 80,000, 90,000, 100,000, 120,000, 130,000, or 140,000 Daltons.

The poly(D,L-lactide-co-glycolide-co-ε-caprolactone) can have a polydispersity index (PDI) that can be less than about 2.0, for example, from about 1.5 to about 1.8.

The poly(D,L-lactide-co-glycolide-co-ε-caprolactone) can have a glass transition temperature ($T_g$) of 30° C. or less, such as from about −20° C. to about 30° C. For example, the poly(D,L-lactide-co-glycolide-co-ε-caprolactone) can have a glass transition temperature ($T_g$) of 30, 25, 22, 21, 20, 15, 10, 5, 0, −5, −8, −9, −10, −12, −15, or −20° C.

The poly(D,L-lactide-co-glycolide-co-ε-caprolactone) can have various mole ratios of lactide:glycolide:caprolactone. For example, D,L-lactide can be present in a mol % ranging from 10 to 60%, glycolide can be present in a mol % ranging from 10 to 50%, and ε-caprolactone can be present in a mol % ranging from 10 to 80%. Table 1 lists mol % compositions for the poly(D,L-lactide-co-glycolide-co-ε-caprolactone)s.

TABLE 1

Mol % compositions poly(D,L-lactide-co-glycolide-co-ε-caprolactone).

| D,L-lactide mol % | Glycolide mol % | ε-caprolactone mol % |
|---|---|---|
| 10 | 10 | 80 |
| 20 | 10 | 70 |

TABLE 1-continued

Mol % compositions poly(D,L-lactide-co-glycolide-co-ε-caprolactone).

| D,L-lactide mol % | Glycolide mol % | ε-caprolactone mol % |
|---|---|---|
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |

A pressure-sensitive adhesive can consist of the terpolymer only or can further comprise other additives. Other additives that can be used to tune the physical properties of the adhesive include humectants such as glycerin or PEG, and plasticizers such as unreacted monomer, i.e. lactide, glycolide, or ε-caprolactone, as well as mineral oil or lanolin.

The terpolymer can be prepared by copolymerizing (ring-opening polymerizing) D,L-lactide, glycolide, and ε-caprolactone in a desired molar ratio using a suitable initiator. A variety of nucleophilic initiators can be used. The initiator can be PEG, mPEG, PPO, PEG/PPO copolymers, fatty alcohols or polyalcoholic species such as glycerin, and saccharides as well as water and glycolic acid. Catalysts can also be used during polymerization, such as stannous octoate. The polymerization can proceed from 8 to 24 hours at from 130° C. to 180° C., after which time any unreacted monomer can be removed under vacuum. A poly(D,L-lactide-co-glycolide-co-ε-caprolactone) of a particular molecular weight can be prepared by using the appropriate amounts of initiator relative to monomer feed, which can control the length of the polymer chains produced.

In one aspect, the terpolymer can be cross-linked with a molecule having 2 or more hydroxyl groups to increase the polymer's cohesive strength. A molecule with multiple hydroxyl groups can be inserted into a polyester backbone via sequential interchange reactions using methods known in the art.

Cohesiveness of the terpolymer can also be improved by sequential copolymerization using an alcohol initiator, e.g. hexanediol, caprolactone, glycolide, and lactide. L-lactide can also be polymerized with caprolactone and glycolide in the solid-state using polyethylene glycol (PEG), methoxypolyethylene glycol (mPEG), polypropylene oxide (PPO), or PEG/PPO macroinitiators.

The poly(D,L-lactide-co-glycolide-co-ε-caprolactone) can be sterilized prior to use, if so desired, for example using γ-ray irradiation at a dosage of about 35 kGy or less, for example, from 22-28 kGy of gamma radiation at a slow dose rate of 4-6 kGy/hour. The irradiation procedure can reduce the molecular weights of the terpolymer. It can thus be useful, in some aspects, to start with terpolymers having a slightly higher (about 10,000 Daltons higher) molecular weight than the final targeted molecular weight of the terpolymer.

(ii) Terpolymer Blend PSA

The terpolymer blend pressure-sensitive adhesive comprises a blend comprising (a) a first poly(D,L-lactide-co-glycolide-co-ε-caprolactone) having a molecular weight (Mw) of from 75,000 to 250,000 Daltons and a polydispersity index (PDI) of less than 2.0, and (b) a second poly(D,L-lactide-co-glycolide-co-ε-caprolactone) having a molecular weight (Mw) of 130,000 Daltons or less and a polydispersity index (PDI) of less than 2.0.

The first poly(D,L-lactide-co-glycolide-co-ε-caprolactone) can be elastomeric or viscoelastic, and the second poly(D,L-lactide-co-glycolide-co-ε-caprolactone) can be tacky or sticky. The blended composition of the first and second polymer thus functions as a pressure-sensitive adhesive, which can adhere to a variety of substrates with the application of light pressure.

The first poly(D,L-lactide-co-glycolide-co-ε-caprolactone) has a molecular weight ($M_w$) of from 75,000 to 250,000 Daltons, and in some embodiments, from 100,000 to 130,000 Daltons. For example, the first poly(D,L-lactide-co-glycolide-co-ε-caprolactone) can have a molecular weight ($M_w$) of 100,000, 110,000, 112,000, 113,000, 115,000, 119,000, or 125,000 Daltons. The second poly(D,L-lactide-co-glycolide-co-ε-caprolactone) can have a molecular weight of 130,000 Daltons or less, and in some embodiments, from 60,000 to 130,000 Daltons. For example, the second poly(D,L-lactide-co-glycolide-co-ε-caprolactone) can have a molecular weight ($M_w$) of 60,000, 70,000, 80,000, 90,000, 100,000, or 120,000 Daltons.

The second poly(D,L-lactide-co-glycolide-co-ε-caprolactone) has a molecular weight (Mw) that can be less than the first poly(D,L-lactide-co-glycolide-co-ξ-caprolactone). The second poly(D,L-lactide-co-glycolide-co-ε-caprolactone) can have a molecular weight ($M_w$) that can be from 10% to 90% of the molecular weight of the first poly(D,L-lactide-co-glycolide-co-ε-caprolactone). For example, the second poly(D,L-lactide-co-glycolide-co-ε-caprolactone) can have a molecular weight ($M_w$) that can be 10%, 20%, 30%, 40%, 50%, 60%, 70%, 80%, or 90% of the molecular weight ($M_w$) value of the first poly(D,L-lactide-co-glycolide-co-ε-caprolactone).

The first and second poly(D,L-lactide-co-glycolide-co-ε-caprolactone)s each have a polydispersity index (PDI) that can be less than about 2.0, and from about 1.5 to about 1.8. The PDI of the first and second polymer can be the same or different.

The first and second poly(D,L-lactide-co-glycolide-co-ε-caprolactone)s both generally have a glass transition temperature ($T_g$) of 0° C. or less, such as from about −20° C. to about 0° C. For example, the first and second poly(D,L-lactide-co-glycolide-co-ε-caprolactone)s can each have a glass transition temperature ($T_g$) that can be the same or different, of 0, −5, −8, −9, −10, −12, −15, or −20° C.

The weight ratio of the first poly(D,L-lactide-co-glycolide-co-ε-caprolactone) to the second poly(D,L-lactide-co-glycolide-co-ε-caprolactone) can range from about 90:10 to about 60:40, for example, 90:10, 80:20, 70:30, or 60:40.

The first and second poly(D,L-lactide-co-glycolide-co-ε-caprolactone)s can have various mole ratios of lactide:glycolide:caprolactone that can be the same or different from one another. For the first (elastomeric) poly(D,L-lactide-co-glycolide-co-ε-caprolactone), D,L-lactide can be present in a mol % ranging from 10 to 60%, glycolide can be present in a mol % ranging from 10 to 60%, and ε-caprolactone can be present in a mol % ranging from 10 to 80%. For the second (tacky) poly(D,L-lactide-co-glycolide-co-ε-caprolactone), D,L-lactide can be present in a mol % ranging from 10 to 60%, glycolide can be present in a mol % ranging from 10 to 50%, and ε-caprolactone can be present in a mol % ranging from 10 to 80%. Tables 2 and 3 list mol % compositions for the first (elastomeric) and second (tacky) poly(D,L-lactide-co-glycolide-co-ε-caprolactone)s.

TABLE 2

Mol % compositions for first (elastomeric) poly(D,L-lactide-co-glycolide-co-ε-caprolactone).

| D,L-lactide mol % | Glycolide mol % | ε-caprolactone mol % |
|---|---|---|
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 60 | 30 | 10 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |
| 40 | 50 | 10 |
| 10 | 60 | 30 |
| 20 | 60 | 20 |

TABLE 3

Mol % compositions for second (tacky) poly(D,L-lactide-co-glycolide-co-ε-caprolactone).

| D,L-lactide mol % | Glycolide mol % | ε-caprolactone mol % |
|---|---|---|
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |

The amount and exact composition of the blend can be altered to maximize compatibility with a substrate of an implant device. For example, the monomer composition of the second (tacky) polymer can be tailored to be more hydrophilic in order to maximize adhesion to a hydrophilic substrate such as titanium or titanium oxide. A more hydrophobic second (tacky) polymer can be used to adhere to a less polar substrate such as parylene or a biodegradable drug eluting strip, such as a strip made from the lactide/glycolide family of biodegradable polymers.

The blends can further comprise other additives. Other additives that can be used to tune the physical properties of the blend include humectants such as glycerin or PEG, and plasticizers such as unreacted monomer, i.e. lactide, glycolide, or ε-caprolactone, as well as mineral oil or lanolin.

The blends can be prepared by mixing the first and second polymers (and any other additives or components) together in a commercial blender, such as a PATTERSON-KELLY blender, under high shear conditions. The blends can also be prepared by reactive extrusion, extrusion mixing, mixing at low shear with the aid of heat, or dry admixing, in addition to high shear blending.

Each terpolymer can be prepared by copolymerizing (ring-opening polymerizing) D,L-lactide, glycolide, and ε-caprolactone in a desired molar ratio using a suitable initiator. A variety of nucleophilic initiators can be used. The initiator can be PEG, mPEG, PPO, PEG/PPO copolymers, fatty alcohols or polyalcoholic species such as glycerin, and saccharides as well as water and glycolic acid or 1-dodecanol. Catalysts can also be used during polymerization, such as stannous octoate. The polymerization can proceed from 8 to 24 hours at from 130° C. to 180° C., after which time any unreacted monomer can be removed under vacuum. A poly(D,L-lactide-co-glycolide-co-ε-caprolactone) of a particular molecular weight can be prepared by using the appropriate amounts of initiator relative to monomer feed, which can control the length of the polymer chains produced.

In one aspect, the first poly(D,L-lactide-co-glycolide-co-ε-caprolactone) can be cross-linked with a molecule having 2 or more hydroxyl groups to increase the polymer's cohesive strength using methods known in the art.

Cohesiveness of the first (elastomeric) polymer can also be improved by sequential copolymerization using an alcohol initiator, e.g. hexanediol, of caprolactone, glycolide, and lactide. L-lactide can also be polymerized with caprolactone and glycolide in the solid-state using polyethylene glycol (PEG), polypropylene oxide (PPO), or PEG/PPO macroinitiators.

The poly(D,L-lactide-co-glycolide-co-ε-caprolactone) blends can be sterilized prior to use, preferably using γ-ray irradiation at a dosage of about 25 kGy. The irradiation procedure can reduce the molecular weights of the polymers in the blend. One can thus start with terpolymers having a slightly higher (about 10,000 Daltons higher) molecular weight than the final targeted molecular weight of each terpolymer in the blend.

In another aspect, the blend comprises (a) a poly(D,L-lactide-co-glycolide-co-ε-caprolactone) having a molecular weight of from 75,000 to 250,000 Daltons and a polydispersity index (PDI) of less than 2.0, and (b) a poly(D,L-lactide-co-glycolide-co-mPEG) having a molecular weight of 25,000 or less and a polydispersity index (PDI) of less than 2.0; wherein the poly(D,L-lactide-co-glycolide-co-mPEG) has a molecular weight ($M_w$) that can be less than the poly(D,L-lactide-co-glycolide-co-ε-caprolactone); and wherein the weight ratio of the poly(D,L-lactide-co-glycolide-co-ε-caprolactone) to the poly(D,L-lactide-co-glycolide-co-mPEG) can be from about 95:5 to about 75:25.

For this blend, the poly(D,L-lactide-co-glycolide-co-ϵ-caprolactone) is described above as the first (elastomeric) polymer. The poly(D,L-lactide-co-glycolide-co-mPEG) can be the tacky component of the blend. The poly(D,L-lactide-co-glycolide-co-mPEG) has a molecular weight ($M_w$) of 25,000 or less, or from 10,000 to 20,000 Daltons. The poly(D,L-lactide-co-glycolide-co-mPEG) has a polydispersity index (PDI) of less than 2.0, or from 1.4 to 1.7. The poly(D,L-lactide-co-glycolide-co-mPEG) has a glass transition temperature ($T_g$) of 0° C. or less, such as from about −20° C. to about 0° C. For example, the poly(D,L-lactide-co-glycolide-co-mPEG) can have a glass transition temperature ($T_g$) of 0, −5, −8, −9, −10, −12, −15, or −20° C.

The weight ratio of the poly(D,L-lactide-co-glycolide-co-ϵ-caprolactone) to the poly(D,L-lactide-co-glycolide-co-mPEG) can range from about 95:5 to about 70:30, for example, 95:5, 90:10, 80:20, or 70:30.

The molar ratio of D,L-lactide to glycolide in the poly(D,L-lactide-co-glycolide-co-ϵ-caprolactone) can range from 90:10 to 40:60, for example, 90:10, 80:20, 70:30, 60:40, 50:50, or 40:60. The polyethylene glycol (mPEG) portion exists as a block on the end of a poly(D,L-lactide-co-glycolide) chain. Such a poly(D,L-lactide-co-glycolide-co-ϵ-caprolactone) is prepared by initiating D,L-lactide and glycolide with an mPEG initiator. Thus, the mPEG portion of the polymer can be defined by the starting mPEG initiator, in terms of molecular weight ($M_w$). The PEG initiators can be obtained commercially, and the molecular weight ($M_w$) of the PEG refers to the molecular weight listed by the commercial supplier. A specific example is mPEG 2000, which has a molecular weight ($M_w$) of about 2000 as listed by the commercial supplier Spectrum Chemicals and Laboratory Products, New Brunswick, N.J.

The poly(D,L-lactide-co-glycolide-co-mPEG) can also be characterized by the molar ratio of lactide, glycolide, and ethylene glycol in the polymer. The lactide mol % can range from 10 to 60%, the glycolide mol % can range from 10 to 60%, and the ethylene glycol can range from 10 to 80%. Table 4 lists mol % compositions for the poly(D,L-lactide-co-glycolide-col-mPEG)s.

TABLE 4

Mol % compositions for poly(D,L-lactide-co-glycolide-co-mPEG).

| D,L-lactide mol % | Glycolide mol % | Ethylene glycol mol % |
| --- | --- | --- |
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 10 | 40 | 50 |
| 20 | 40 | 40 |
| 30 | 40 | 30 |
| 40 | 40 | 20 |
| 50 | 40 | 10 |
| 10 | 50 | 40 |

TABLE 4-continued

Mol % compositions for poly(D,L-lactide-co-glycolide-co-mPEG).

| D,L-lactide mol % | Glycolide mol % | Ethylene glycol mol % |
| --- | --- | --- |
| 20 | 50 | 30 |
| 30 | 50 | 20 |

Alternatively, the poly(D,L-lactide-co-glycolide-co-mPEG) can be characterized by its molar percentages and lactide and glycolide and by the molecular weight of the mPEG block. In certain aspects, the polymer can comprise from 50 mol % DL-lactide to 100 mol % DL-lactide and less than or equal to 50 mol % glycolide for a family of mPEG-based terpolymers wherein the $M_w$ of the mPEG portion ranges from about 350 to 5000 Daltons (based on the molecular weight of the starting mPEG initiator).

The poly(D,L-lactide-co-glycolide-co-mPEG) can be made using the methods discussed above. D,L-lactide and glycolide are copolymerized using a mPEG initiator which has a nucleophilic end group. mPEGs are commercially available with an alcohol endgroup, which can initiate the ring-opening polymerization of D,L-lactide and glycolide. The polymerization can be carried out in the presence of a catalyst as discussed above.

Bioactive Agent

As used herein, the term "bioactive agent" refers to a wide range of biologically active materials that causes a biological effect when administered in vivo to an animal. The term "bioactive agent" includes hydrophobic and hydrophilic molecules, including, but not limited to, macromolecules (i.e., molecules with a molecular weight of at least about 1000 Da) such as peptides, proteins, carbohydrates, nucleic acids, lipids, polysaccharides or combinations thereof; or synthetic or natural organic or inorganic molecules. The term "animal" includes, but is not limited to, birds and mammals, including humans. A comprehensive listing of bioactive agents can be found in The Merck Index, Thirteenth Edition, Merck & Co. (2001), the entire contents of which is incorporated by reference herein.

The concentration of bioactive agent within the bioactive layer and/or PSA layer can vary depending upon a variety of factors, including the agent and its intended use, i.e. short or long duration. In one aspect, the bioactive agent can be present in an amount ranging from 0.05% to 80% by weight of the implant, for example, 0.1%, 0.5%, 5%, 10%, 15%, 20%, 30%, 40%, 45%, 50%, 55%, 60%, 70%, or 80%.

Examples of bioactive agents that can be incorporated into either the bioactive layer or PSA include immunostimulating agents, antiviral agents, antikeratolytic agents, anti-inflammatory agents, antifungal agents, acne treating agents, sunscreen agents, dermatological agents, antihistamine agents, antibacterial agents, antiviral agents, respiratory burst inhibitors, inhibitors of prostaglandin synthesis, antimicrobial agents, antifungal agents, antiseptic agents, anesthetic agents, cell nutrient media, burn relief medications, sun burn medications, insect bite and sting medications, wound cleansers, wound dressings, scar reducing agents, and mixtures thereof, in an amount from about 0.05% to about 10%, by weight. In a further aspect, one or more of any bioactive agent can be incorporate d into either the bioactive layer or PSA.

In a further aspect, bioactive agent can include one or more anti-inflammatory agent including, but not limited to, ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone diproprionate, betamethasone diproprionate, hydrocortisone, cortisone, dexamethasone, predinisone, methyl prednisolone, and prednisolone; in an amount from about 0.05% to about 10%, by weight.

In yet a further aspect, the bioactive agent can include one or more antioxidant. Representative antioxidants that can be used as bioactive agents include, but are not limited to, all forms of Vitamin A including retinal and 3,4-didehydroretinol, all forms of carotene such as Alpha-carotene, β-carotene (beta, t-carotene), gamma-carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopy ran-6-ol), β-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, β-carotene, Vitamin E, Vitamin E acetate, and mixtures thereof. More preferably, the antioxidant is Vitamin E or Vitamin E acetate. Most preferably, the antioxidant is Vitamin E acetate, in an amount from about 0.05% to about 10%, by weight.

In a further aspect, other bioactive agents can include, but are not limited to, anti-viral agents such as acyclovir, foscarnet sodium, ribavirin, vidarabine, ganeiclovir sodium, zidovudine, phenol, amantadine hydrochloride, and interferon alfa-n3, in an amount from about 0.05% to about 10%, by weight. In yet a further aspect, the bioactive agent can include, but it not limited to, an anti-fungal agent such as lactic acid, sorbic acid, miconazole, clotrimazole, tioconazole, terconazole, povidone-iodine, and butoconazole, in an amount from about 0.05% to about 10%, by weight. In another aspect, the bioactive agent can include, but is not limited to, an anti-bacterial agent such as silver compounds, such as silver chloride and colloidal silver, bismuth compounds, such as bismuth aluminate, bismuth subcitrate, bismuth subgalate, bismuth subsalicylate; the sulfonamides; the nitrofurans, such as nitrofurazone and nitrofurantoin; furazolidone, metronidazole, tinidazole, nimorazole, benzoic acid, the aminoglycosides; such as gentamicin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and chloramphenicol, and clidamycin. In yet a further aspect, the bioactive agent can be an anti-microbial agent, including, but not limited to, such as benzalkonium chloride, chlorhexidine gluconate, thimerosal sodium, chlorobutanol and phenylmercuric acetate glyceryl monolaurate, propyl p-hydroxybenzoate, chlorhexidine gluconate, sodium lactoyl caprylate, benzyl alcohol, imidazolidinyl urea, trichlorocarbonilide, and zinc undecylenate, in an amount from about 0.05% to about 10%, by weight.

In a further aspect, the bioactive agent can include, but is not limited to, one or more quanternay ammonium compounds. Such compounds can include or more of the following: alkyl dimethylbenzylammonium chloride, benzalkonium bromide, benzalkonium chloride, benzalkonium fluoride, alkylbenzyldimethylammonium chloride, alkyldimethylbenzylammonium chloride, n-alkyldimethylbenzylammonium chloride, diisobutylphenoxyethoxyethyl dimethylammonium chloride, n-dimethylbenzylammonium chloride, octyldecyldimethylammonium chloride, didecyldimethylammonium chloride, dioctyldimethylammonium chloride, diaklyldimethylammonium chloride, octyldecyldimethylammonium chloride, laurryl dimethylbenzylammonium chloride, o-benzyl-p-chlorophenol, diethyldimethylammonium chloride, doctyldimethylammonium chloride, alkyldimethylbenzylammonium chloride, and alkylbenzyldimethylammonium chloride, in an amount from about 0.05% to about 10%, by weight.

In yet a further aspect, the bioactive agent can include, but not limited to, one or more of an enzyme inhibitor. Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, 1-hydroxymaleate, iodotubercidin, p-bromotetramisole, 10-Calpha.-diethylaminopropionylyphenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl.HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacin, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

In a further aspect, the bioactive agent can include, but not limited to, one or more of a cell response modifier. Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, estradiols, insulin-like growth factor, nerve growth factor, bone growth/cartilage-inducing factor (alpha and beta), and matrix metallo proteinase inhibitors. Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin. Vascular endothelial growth factor (VEGF) is a chemical signal produced by cells that stimulates the growth of new blood vessels. VEGF inhibitors can be used to treat diseases such as cancers, which require an adequate blood supply to grow and metastasize. DNA that encodes for the production of any of these proteins, antisense molecules, androgenic receptor blockers and statin agents can also be a bioactive agent.

For the uses below, any of the terpolymers or terpolymer blends disclosed above can be used. In a further aspect, a pressure-sensitive adhesive can comprise any the terpolymer or terpolymer blends disclosed above.

Article Comprising a Conformable Backing Member

In one aspect, the article comprises a conformable backing member and a coating covering at least a portion of one major surface thereof of a pressure-sensitive adhesive (PSA) comprising or consisting of any of the terpolymers disclosed above. In a further aspect, the PSA can optionally comprise a bioactive agent. In a further aspect, the conformable backing member is coated with a bioactive layer comprising a biodegradable polymer matrix and a bioactive agent. In yet a further aspect, the PSA surface can be adhered to the surface of a release liner.

Figure 2:
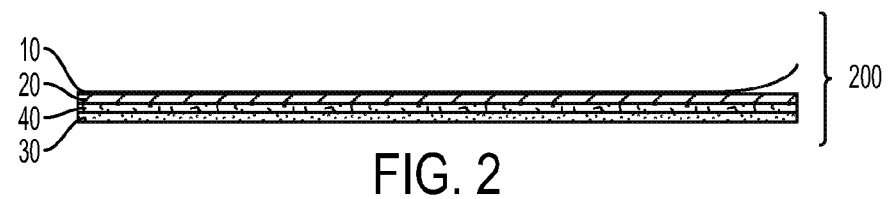
FIG. 2 is a schematic illustration of an article comprising conformable backing member coated with a bioactive layer which is coated pressure-sensitive adhesive adhered to a release liner.
Figure 3:
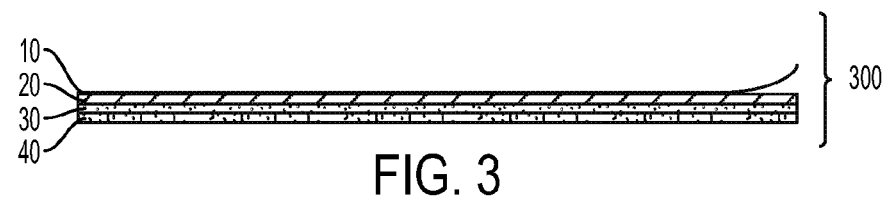
FIG. 3 is a schematic illustration of an article comprising conformable backing member coated with a bioactive layer on one side and a pressure-sensitive adhesive on the other side adhered to a release liner.

In one aspect, as shown in FIG. 1, the article 100 comprises a release liner 10 adhering to the PSA 20 which is coated or applied to the conformable backing member 30. In another aspect, as shown in FIG. 2, the article 200 comprises a release liner 10 adhering the PSA 20 which is coated or applied to the bioactive layer 40 which is coated or applied to the conformable backing member 30. In yet another aspect, as shown in FIG. 3, the article 300 comprises a release liner 10 adhering the PSA 20 which is coated or applied to the conformable backing member 30 to which the bioactive layer 40 which is coated or applied, on the reverse side of the conformable backing member to the PSA layer.

The article can have any desired shape. A planar article can be substantially square, rectangular, circular, triangular, among other shapes. In one aspect, the article can be square or rectangular. In a further aspect, the article has a shape that can be non-rectangular.

The articles can have any desired size. When the pressure-sensitive adhesive comprises a bioactive agent, the size selection of the article can be influenced by the desired loading of the bioactive agent. Generally, the more bioactive agent that can be desired, the larger the article will be. The size can also be selected so as to provide the desired release properties of the pressure-sensitive adhesive film. It can be desirable for portions of the conformable backing surface to remain exposed. In these instances, the size of the pressure-sensitive adhesive can be selected so as to not completely cover the conformable backing surface.

The pressure-sensitive adhesive can have any desired thickness. In one aspect, the pressure-sensitive adhesive can be a thin film having a thickness of from about 1 nm, or less, to about 1000 nm, including without limitation those films having thicknesses of about 5 nm, 20 nm, 50 nm, 100 nm, 150 nm, 200 nm, 300 nm, 500 nm, 800 nm, or 900 nm. In a further aspect, the film has a thickness greater than about 1000 nm, including without limitation those films having thicknesses of from about 1000 nm to about 50 microns, or greater. For example, the film can have a thickness of about 1 µm, 5 µm, 20 µm, 30 µm, 40 µm, or 50 µm. It is to be understood that the film does not have to be, but can be, planar. Thus, in various aspects, the film can have varying heights at different regions of the film. As such, the film can comprise any shape, as discussed above, depending on the desired shape of the article.

Any suitable release liner can be used. The release liner can be a temporary release liner that can be removed from the pressure-sensitive adhesive of the article prior to the article being implanted into a subject or prior to being applied to an implant device. As such, it can be useful if the temporary release liner not leave behind any material in a quantity that could be harmful to a subject.

Suitable release liners are those that are made of materials that permit the release liner to be easily stripped or peeled away from the adjacent pressure-sensitive adhesive. Exemplary release liners are those that are comprised of paper and/or a plastic material. Typically, such release liners are made from polymers such as polyesters or polyethylenes which are coated with materials such as silicone or fluorinated hydrocarbons that reduce the adhesiveness between the release liner and the adjacent adhesive. Other suitable release liners include paper, such as kraft paper, that can be covered with a silicone material, which permits the easy release of the liner from the adhesive. Release liner materials are available commercially, for example, polyethylene is commercially available from 3M®.

The PSA compositions prepared as described above are easily coated upon suitable conformable backing materials by conventional coating techniques to produce skin adhesive coated sheet materials in accordance with the present invention. Suitable backings include any of the well-known backings which find use in medical or surgical fields. Typical examples of conformable backing materials which can be useful for the adhesive compositions of the present invention include those made of nonwoven fabric, woven fabric, knit, or medium to low tensile modulus synthetic films such as polypropylene, polyethylene, polyvinyl chloride, polyurethane, low modulus polyester, and ethyl cellulose. With respect to the conformable synthetic film backings, the film should have a tensile modulus of less than about 400,000 psi as measured in accordance with ASTM D-638 and D-882, preferably less than about 300,000 psi.

In one aspect, the PSA coated conformable backing member comprises sheet materials. The sheet material can be applied to an internal body surface, such as a tissue or bone, or to an external body surface, such as skin or a wound. In yet a further aspect, at least one face of the sheet material is covered in its entirety with PSA. In a further aspect, the PSA is coated on the edges on the sheet material forming a border containing an inner area. The width of the PSA along the edges will be determined by one skilled in the art as necessary for the appropriate adherence to the external body surface. In another aspect, the inner area comprises a bioactive layer.

In one aspect, the conformable backing member comprises backings. Backings can also be prepared of fabric such as woven fabric formed of threads of synthetic or natural materials such as cotton, nylon, or rayon, and the like or nonwoven fabric such as air laid webs of natural or synthetic fibers or blends of these. In yet a further aspect, are those which permit transpiration of perspiration and/or tissue or wound exudate therethrough, e.g., nonwoven fabrics, woven fabrics, knits and the like. In another aspect, the backing can be biodegradable or non-biodegradable. The term "biodegradable polymer matrix" refers to a material that is fully degraded and absorbed in vivo in the mammalian body. Suitable non-biodegradable polymers include common textile materials such as cellulose processed cellulose such as viscose, polyamide, polyurethane, and also alginates. Suitable biodegradable polymers include those consisting of collagens, bioabsorbable cellulose derivatives such as oxidized celluloses, galactomannans such as guar/borate, glycosaminoglycans such as cross-linked hyaluronates, polylactides/polyglycolides, polyhydroxybutyrates, and mixtures thereof. In a further aspect, the biodegradable polymer matrix comprises poly(D, L-lactide-co-glycolide) polymers. In yet a further aspect, the poly(D,L-lactide-co-glycolide) polymer has a molecular weight of about 20,000 Daltons or less.

In certain aspects, the backings are, accordingly, moisture vapor permeable in that they have a high rate of transmission of moisture vapor therethrough. In another aspect, the backings have moisture vapor transmission values, when tested in accordance with ASTM E 96-80, of at least about 500 g/m², over 24 hours at 100° F. (38° C.) with a humidity differential of 80%, more preferably at least about 1000 g/m2. For example, a continuous film backing prepared from a polyurethane sold under the tradename Estane, available from B. F. Goodrich, and a continuous film backing prepared from a polyester sold under the tradename Hytrel, available from DuPont, each have values of about 1000 to about 1500 g/m² and woven backings such that those used for DURAPORE® tape, available from 3M, have even higher values. In contrast, conventional polyethylene terephthalate films have approximate values of about 50 g/m².

The conformable backing member and a coating covering at least a portion of one major surface thereof of a pressure-sensitive adhesive (PSA) comprising or consisting of any of the terpolymers disclosed above can take the form of any article conventionally known to be utilized with skin adhesives such as tapes, patches, strips, wound dressings, monitoring or neuro-stimulating electrodes, drapes or the like. These articles can be dispensed from any convenient dispensing form, e.g., multi-layered pads, rolls, and the like.

The pressure sensitive adhesive compositions of the present invention can be coated by any of a variety of conventional coating techniques such as roll coating, spray coating, curtain coating, and the like. As is known to those skilled in the art, the particular method selected can depend upon the nature of the backing being employed. For example, where the backing is a nonwoven fabric, a suitable method for applying the adhesive copolymer thereto involves coating a solution of the adhesive copolymer in an organic solvent onto a release liner, followed by lamination of the nonwoven fabric backing to the (semi-dry) adhesive coating. The compositions can also be coated without modification by extrusion coating, coextrusion, hot-melt coating and the like by employing suitable conventional coating devices for this purpose. Primers can be used but they are not always necessary.

The pressure sensitive adhesive compositions of this invention can also be used in a method of adhering a substrate to skin. In this method an effective amount of a pressure sensitive adhesive of this invention is interposed between the substrate and skin and pressure is applied to activate the pressure sensitive adhesive. The substrate is preferably a sheet material as described above which is applied to the skin as a cover, patch or tape for the conventional purposes thereof.

Envelope for Delivery of Therapeutic Materials

In one aspect, the PSA coated conformable backing member comprises sealable packages for delivery of therapeutically useful materials to or within the body of animal. In a further aspect, the animal is human. In yet a further aspect, the package is sealed with the PSA described above. In yet a further aspect, the surface areas of the packaging comprise a biocompatible material. In a further aspect, the biocompatible material is biodegradable. In yet a further aspect, the seams or edges of the package are held together with the PSA described above. In a further aspect, the package is formed as an envelope.

Figure 6:
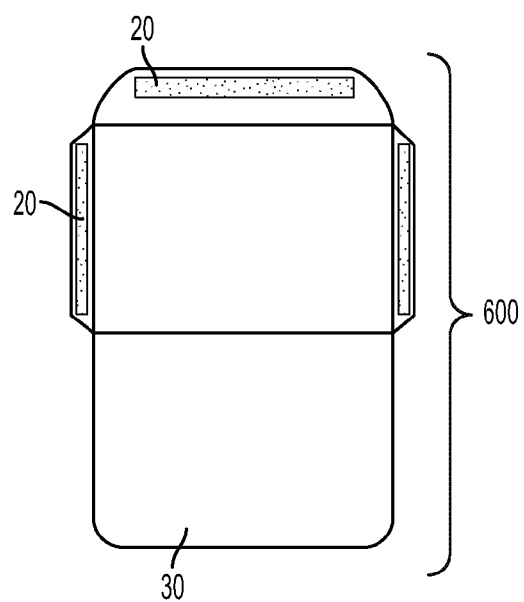
FIG. 6 is a schematic illustration of an article shaped to form an envelope structure when folded.
Figure 7:
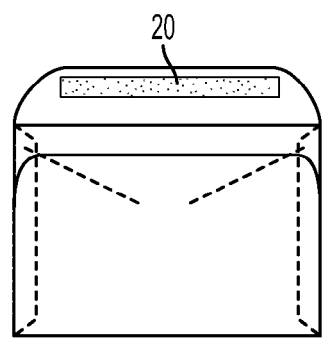
FIG. 7 is a schematic illustration of an article form into an envelope structure.

In yet a further aspect, the article 600, as shown in FIG. 6, is shaped so that it can be formed into an envelope. The sheet material can be biodegradable or non-biodegradable as required by the medical application. The PSA 20 is coated in discrete locations that form flaps that when folded as shown in FIG. 7 form an envelope. The cavity of the envelope can contain with a liquid or gel added at the time use wherein the liquid or gel comprises a bioactive agent. In a further aspect, the envelope contains a liquid or gel added during production and the last flap is sealed, thus forming a sealed package. In a further aspect, the article 600 is coated with a bioactive layer on at least one surface and the PSA coated over the bioactive layer in discrete locations as indicated in FIGS. 6 and 7. In yet a further aspect, a release liner is adhered to the PSA layer.

In one aspect, the envelope is placed in contact with bodily fluids wherein the envelope is sealed with the PSA described above. Upon disposition within the body, in contact with bodily fluids, the PSA envelope seal undergoes biodegradation thereby providing bodily access to the contents of the envelope. In a further aspect, the contents are a gel or liquid comprising a bioactive agent. The bioactive agent can comprise one or more of the bioactive agents described above.

Medical Wrapping Material

In one aspect, article comprises a PSA coated conformable backing member wherein the conformable backing member comprises sheet materials. In a further aspect, the sheet material can be applied to an internal body surface, such as a tissue or bone. In yet a further aspect, at least one face of the sheet material is covered in its entirety with PSA. In a further aspect, the PSA is coated on the edges on the sheet material forming a border containing an inner area. The width of the PSA along the edges will be determined by one skilled in the art as necessary for the appropriate adherence to the external body surface. In another aspect, the inner area comprises a bioactive layer.

In one aspect, the tissue contacted is a bowel which has undergone surgical resectioning wherein the edges of the cut bowel are held together, at least in part, by PSA coated sheet material wrapped around the edges of the bowel brought into contact with one another. In a further aspect, the bone contacted is fractured, broken, or in need to repair or support, is wrapped with the PSA coated sheet material to provide support, at least in part, to the portion of bone requiring repair.

Figure 4:
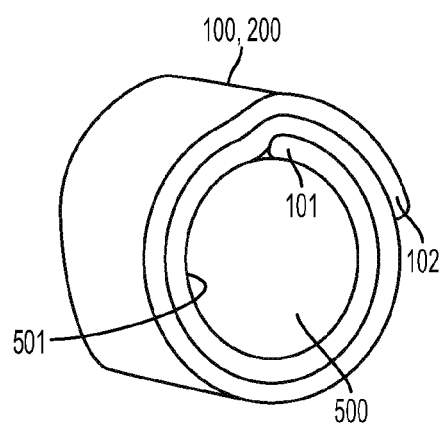
FIG. 4 is a schematic illustration of an article applied to a tissue or bone.
Figure 5:
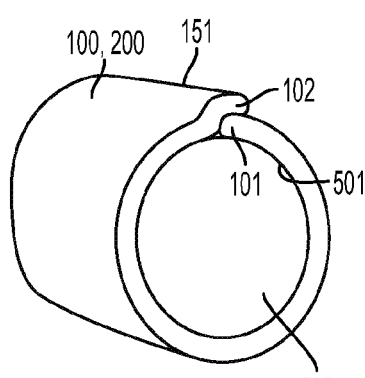
FIG. 5 is a schematic illustration of an article applied to a tissue or bone.

In yet a further aspect, the medical pressure sensitive adhesive coated sheet material is wrapped around the target internal surface such that the sheet material makes contact with the initial portion of itself. In a further aspect, as shown in FIG. 4, the article 100 or 200 is wrapped around a surface 501 of an underlying tissue or bone 500 to form multiple layers. In general, as the length L of the article 100 or 200 applied to the tissue or bone 500 increases, the amount of bioactive agent. In yet a further aspect, as shown in FIG. 5, the article 100 or 200 is wrapped around a surface 501 of the underlying tissue or bone 500 to form essentially a single layer. It should be understood that the term "single layer" is meant to allow for overlap 151 between first 101 and second 102 ends of the article 100.

Biodegradable Packaging

In one aspect, the article relates to the fabrication of biodegradable articles comprising coating a biodegradable polymer with the PSA. These biodegradable articles include, but are not limited to, sanitary and/or medical garments, that include sanitary napkins, wipes, diapers, diaper topsheets, diaper backsheets, disposable garments, medical disposables, disposable wipes, pantyliners, binders for cellulose fibers or synthetics, and the like, as well as compostable bags such as shopping and lawn/leaf bags, agricultural films, fishing nets, yard waste nets and seeding templates.

Suitable substrates include paper, fabric, thread and yarn. Often the substrate will be paper. As used herein, "paper" refers to a substrate formed from cellulose fiber, including paper and cardboard. As used herein, "fabric" includes natural and synthetic fabrics. The fabrics can be knitted, woven or non-woven. Suitable fabrics include cotton, rayon, wool, and polyesters, as well as biodegradable fabrics comprising polyhydroxyalkanoate polymers (PHAs"). As used herein, "thread and yarn" includes natural and synthetic threads and yarns, such as cotton, rayon, polyester, wool, silk, nylon, and acrylic as well as biodegradable threads and yarns comprising PHAs. Thread and yarn can be formed using fibers of PHA. As used herein, "fiber" refers to a flexible, macroscopically homogeneous body having a high length-to-width ratio and a small cross section.

Coated paper can be used as backing for tape; preferably the tape comprises paper, a coating comprising PSA and an adhesive, preferably an adhesive comprising PSA.

Fabric and paper coated with PSA can be used to form items such as wrapping paper, paper bags, plastic bags, cardboard containers, drink boxes, trays, table clothes, napkins, rain coats and ponchos, and disposable garments such as surgical scrubs. Disposable garment seams can be sewn with a PSA-coated thread, or can be joined with an adhesive, preferably a biodegradable adhesive comprising a PSA.

In a further aspect, the article comprises a diaper wherein the seams, edges, and adherable surfaces comprise coating with a PSA described above. In a further aspect, the diaper comprises fibers coated with a PSA describe above. In yet a further aspect, the diaper itself comprises materials that are biodegradable. In a further aspect, the diaper itself comprises materials that are compostable. In still a further aspect, the diaper is biodegradable and/or compostable.

In yet a further aspect, the article comprises compostable packaging wherein the seams, edges, and adherable surfaces of the packaging are coated with a PSA described above. The compostable packing includes, but is not limited to, landscape matting, sacks, or grocery bags, garbage bags, both food and nonfood packaging, or as backsheets in articles such as diapers, sanitary napkins, pantyliners, and the like, which are adapted for absorbing various bodily fluids. Paper can be coated with the PSA described above.

Medical Dressings

In one aspect, the article comprises PSA further comprising a bioactive agent coated onto a conformable backing member wherein the conformable backing member comprises a disposable, polymeric product wherein the polymeric product consists essentially of natural polymers, man-made polymers and mixtures thereof in the form of fibers, yarns, woven, non-woven, and knitted fabrics, sheets and films. In a further aspect, natural polymers can include cotton, linen, or silk. In yet a further aspect, man-made polymers can include viscose rayon, cellulose triacetate, polypropylene, polyethylene and nylon and blends thereof. In further aspect, synthetic or natural polymeric products can include, but are not limited to, polyurethanes, polycarbonates, polyesters, polyamides, polyimides, polyvinyls, polyolefins, Teflon™, Gore-Tex™, polyvinyl alcohols, polyethyleneoxides, polyacrylates, -methacrylates and -cyanoacrylates, latex, polyvinyl chlorides, polylactic and polyglycolic acid derivatives, hydrogel forming agents such as PHEMA, polyethylene oxides, hyaluronic acid, chitosan, alginate, cellulose, and other equivalents known to persons skilled in the art. Each natural or synthetic fibers composing the conformable backing member of interest can be formed as individually spun fibers, as fiber bundles, as twisted cables, as wovens, as nonwovens, as knitted, as knotted, or any equivalents, and any combinations thereof.

In a further aspect, the article is formed, shaped or fabricated to provide sterile wound dressings, drainage materials, pads, patches, band aids, gauze, foams, sponges and so forth, can be manufactured or derived from a combination of modified natural products and synthetic. In a further aspect, the disposable, polymeric product is gauze comprising natural polymers or man-made polymers. In a further aspect, the gauze is coated with the PSA described above.

In a further aspect, the article comprises a bioactive agent which comprises one or more of an anti-microbial, anti-viral, anti-bacterial or anti-fungal agent. In a further aspect, the anti-microbial, anti-viral, anti-bacterial or anti-fungal agent includes, but is not limited to, a bioactive agent described above. In yet a further aspect, the PSA comprises one or more of one or more of an anti-microbial, anti-viral, anti-bacterial or anti-fungal agent. In a further aspect, the PSA comprises an anti-microbial. In yet a further aspect, the article is used to treat an ulcer. In a further aspect, the ulcer is a venous ulcer, an arterial ulcer, a neuropathic ulcer, a pressure ulcer or decubitus ulcer. In yet a further aspect, the article is used to treat a decubitus ulcer.

In a further aspect, the article comprises a bioactive agent wherein the bioactive agent impregnates one or both of the conformable backing member and the PSA coated onto the conformable backing member. In yet a further aspect, the conformable backing member is gauze, a sheet material with absorbent properties, a patch or the like wherein the conformable backing member is impregnated with a bioactive agent. In a further aspect, the PSA comprises a bioactive agent. In yet a further aspect, the bioactive agent comprises one or more of an anti-microbial, anti-viral, anti-bacterial or anti-fungal agent. In a further aspect, the anti-microbial, anti-viral, anti-bacterial or anti-fungal agent, includes, but is not limited to, a bioactive agent described above. In a further aspect, the PSA comprises impregnation with an anti-microbial, anti-viral, anti-bacterial or anti-fungal agent. In yet a further aspect, the PSA comprises chlorhexidine gluconate.

In a further aspect, the article comprises PSA comprising an enzyme inhibitor. In yet a further aspect, the enzyme inhibitor includes, but is not limited to, a bioactive agent described above. In a further aspect, the enzyme inhibitor aids, accelerates or facilitates the process of wound healing. In yet a further aspect, the article is placed upon a wound or injury to increase wound healing.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The following analytical methods were used in all examples, unless indicated otherwise. The inherent viscosity was measured at 0.5% (wt/vol) terpolymer in chloroform at 30° C. using a Cannon-Fenske size 25 viscometer. Polymer composition was determined from $^1$H-NMR spectra recorded in $CDCl_3$ on a Varian Inova spectrometer at 399.85 MHz. Thermal properties were determined using a TA Instruments Differential Scanning calorimeter (DSC) 2920 with Refrigerated Cooling System (RCS). The thermal history was removed by an initial heat ramp. The glass transition temperature ($T_g$) was determined from the DSC curve obtained from a temperature scan rate of 10° C./minute over a temperature range of about −60° C. to 90° C. Gel permeation chromatography (GPC) analyses were performed on a Perkin Elmer Series 200 GPC/RI fitted with a Waters Styragel HR-2 and two Waters HR-5E columns, using chloroform as the mobile phase, and calibrated with multiple polystyrene standards of narrow molecular weight distribution.

Example 1

Single-Component PSA

A resin kettle under a nitrogen blanket inlet, was charged with 262.0 grams (1.818 mol) of D,L-lactide, 141.0 grams (1.215 mol) of glycolide and 347.5 grams (3.045 mol) of ε-caprolactone. The mixture was heated to 140° C. and 2.2793 grams (12.233 mmol) of 1-dodecanol was added. After thorough mixing, the mixture was charged with 228 milligrams (0.562 mmol) of the catalyst stannous octoate. The polymerization proceeded for 18 hours at 170° C. followed by a 2 hour vacuum strip at 28.5 inches Hg vacuum to remove un-reacted monomer. The resulting polymer was poured into a Teflon lined tray, cooled under vacuum and stored at 4° C.

The composition, inherent viscosity Tg and polydispersity were determined: D,L-lactide:glycolide:ε-caprolactone mole ratio (28:21:51); Residual monomer: D,L-lactide (2.2 wt %), glycolide (0.1 wt %), ε-caprolactone (0.5 wt %); Intrinsic Viscosity (IV)=0.87 dL/g; $T_g$=−13.7° C.; $M_w$=116,000, $M_n$=67,000, polydispersity index (PDI)=1.7.

Example 2

Terpolymer Blend PSA

An elastomeric terpolymer poly(D,L-lactide-co-glycolide-co-ε-caprolactone) with a D,L-lactide to glycolide to ε-caprolactone molar ratio=30:20:50 was made by a ring-opening polymerization process using glycolic acid as the initiator and D,L-lactide, glycolide aid ε-caprolactone as the monomer feed. A thoroughly dried resin kettle equipped with a nitrogen inlet, air-cooled distillation adapter with trap, and mechanical stirrer was charged with 261.5 grams (1.814 mol) of DL-lactide (Ortec, South Carolina) and 142.5 grams (1.228 mol) of glycolide (Ortec, South Carolina). The monomer was blanketed with nitrogen and melted at 140° C. 347.2 grams (3.042 mol) of ε-caprolactone (Ortec, South Carolina) and 1.393 grams (18.31 mmol) of the initiator glycolic acid (Sigma-Aldrich, Wisconsin) was added. After thorough mixing, the mixture was charged with 223 milligrams (0.550 mmol) of the catalyst stannous octoate (Sigma-Aldrich, Wisconsin). The polymerization proceeded for 18 hours at 170° C. followed by a 2 hour vacuum strip at 28.5 in HG vacuum to remove un-reacted monomer. The final terpolymer was comprised of 30 mol % D,L-lactide, 22 mol % glycolide and 48 mol % ε-caprolactone as determined by proton NMR. The polymer had an inherent viscosity (IV) of 0.84 dL/g and a $T_g$ of −12° C. The number and weight average molecular weights were $M_n$=73,000 and $M_w$=119,000, respectively.

A terpolymer (302050 DLGCL 6A) was made via the same ring-opening polymerization route described in Example 1 using 174.4 grams (1.210 mol) of DL-lactide (Ortec, South Carolina) and 94.3 grams (0.813 mol) of glycolide (Ortec, South Carolina). The monomer was blanketed with nitrogen and melted at 140° C. 231.7 grams (2.030 mol) of ε-caprolactone (Ortec, South Carolina) and 0.933 grams (12.3 mmol) of the initiator glycolic acid (Sigma-Aldrich, Wisconsin) was added. After thorough mixing, the mixture was charged with 147 milligrams (0.364 mmol) of the catalyst stannous octoate (Sigma-Aldrich, Wisconsin). The mole percent of DL-lactide, glycolide and ε-caprolactone in the polymer was 29%, 21% and 50%, respectively, The IV was 0.55 dL/g and the Tg-15° C. The number and weight average molecular weights were Mn=39,000 and Mw=65,000.

A terpolymer (5050 DLG mPEG 2K) was made via a ring-opening polymerization using mPEG 2000 as the initiator and DL-lactide and glycolide as the monomer feed similar to that described in Example 1. The polymerization took place in a reactor that was placed in a force-air oven set to 150° C. without mixing. To the reactor was charged 111.9 grams (0.776 mol) of DL-lactide (Ortec, South Carolina), 86.5 grams (0.745 mol) of glycolide (Ortec, South Carolina) and 101.7 grams of dry mPEG 2000 (0.051 mol; Spectrum Chemicals and Laboratory Products, New Brunswick, N.J.) to which 0.150 grams (0.370 mmol) of the catalyst stannous octoate (Sigma-Aldrich, Wisconsin) was added. The mole percent of DL-lactide, glycolide and ethylene glycol in the polymer was 20%, 20% and 60%, respectively. The IV was 0.19 dL/g and the Tg=−9° C. The number and weight average molecular weights were $M_n$=10,000 and $M_w$=14,000.

Any of the above described terpolymers can be blended together to create a terpolymer blend functioning as a PSA.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

Example 3

Preparation of Polymer and Formulation for Bioactive Layer

A resin kettle under a nitrogen blanket was charged with 605.2 grams (4.199 mol) of D,L-lactide and 146.0 grams (1.258 mol) of glycolide and was heated to 140° C. 1-dodecanol (42.28 grams; 226.9 mmol) and 240 milligrams (0.592 mmol) of the catalyst stannous octoate was subsequently added. The polymerization was allowed to proceed for 4 hours at 170° C. followed by a 2 hour vacuum strip at 28.5 inches of Hg vacuum to remove un-reacted monomer. The resulting polymer was poured into a Teflon lined tray filled with liquid nitrogen and stored at 4° C. The polymer was cryo-milled with a bench top Stephan Mill and stored at 4° C.

The resulting polymer was found to have the following properties. The D,L-lactide:glycolide mole ratio was 76:24. The composition comprised residual D,L-lactide in an amount of 2.1 wt. %, and residual glycolide in an amount of 0.1 wt. %. The polymer had an intrinsic viscosity (IV)=0.14 dL/g, $T_g$=25.4° C., $M_w$=11,000, $M_n$=6,000, and polydispersity index (PDI=1.8).

A formulation of bioactive agent and the poly(D,L-lactide-co-glycolide) discussed above was prepared. The poly(D,L-lactide-co-glycolide) and bioactive agents Minocycline and Rifampin were added to a mixed solvent system of Acetone (68% w/w) and Methanol (32%, w/w) to provide a composition having 68% poly(D,L-lactide-co-glycolide), 12% Minocycline, and 20% Rifamcin (all % by weight). The overall solids concentration was 300 mg/mL (36 mg/mL Minocycline, 60 mg/mL Rifampin, and 204 mg/mL poly(D,L-lactide-co-glycolide).

Example 4

Anti-Microbial Carrier

The PSA is coated onto a matrix made of cotton gauze 75 mm wide. The PSA comprises 0.5% (wt/wt) chlorohexidine gluconate. The antimicrobial activity of the product is tested on lawns of several bacteria: *Staphylococcus aureus* (SA), *S. epidermidis* (SE), *Escherichia coli* (EC) and *Pseudonomas aeruginosa* (PA), inoculated on agar plates, by placing a sample of about 2 cm$^2$ on the surface of the plate, and measurement of the inhibition zone after growth of the bacterial for 18 hours at 37° C. After 24 hours, the sample is passed sequentially to another inoculated agar plate and the inhibition zone measured. This daily transfer procedure is continued up to the loss of growth-inhibiting activity.

Example 5

Anti-Microbial Carrier

The PSA is coated onto a matrix made of medical grade woven polyethylene. The PSA comprises 0.5% (wt/wt) chlorohexidine gluconate. The antimicrobial activity of the product is tested on lawns of several bacteria: *Staphylococcus aureus* (SA), *S. epidermidis* (SE), *Escherichia coli* (EC) and *Pseudonomas aeruginosa* (PA), inoculated on agar plates, by placing a sample of about 2 cm$^2$ on the surface of the plate, and measurement of the inhibition zone after growth of the bacterial for 18 hours at 37° C. After 24 hours, the sample is passed sequentially to another inoculated agar plate and the inhibition zone measured. This daily transfer procedure is continued up to the loss of growth-inhibiting activity.

Example 6

Anti-Microbial Carrier

The PSA is coated onto a matrix made of medical grade cotton gauze. The PSA comprises 0.5% (wt/wt) chlorohexidine gluconate. The antimicrobial activity of the product is tested on lawns of several bacteria: *Staphylococcus aureus* (SA), *S. epidermidis* (SE), *Escherichia coli* (EC) and *Pseudonomas aeruginosa* (PA), inoculated on agar plates, by placing a sample of about 2 cm$^2$ on the surface of the plate, and measurement of the inhibition zone after growth of the bacterial for 18 hours at 37° C. After 24 hours, the sample is passed sequentially to another inoculated agar plate and the inhibition zone measured. This daily transfer procedure is continued up to the loss of growth-inhibiting activity.

Example 7

Medical Envelope

The PSA comprising 0.5% (wt/wt) doxycline is coated onto the flaps of Surgicel Absorbable Hemostat® that is cut in the shape shown FIG. 6. The article is formed into an envelope as shown in FIG. 7, and the cavity is filled with phosphate-buffered saline comprising 0.5% doxycline. The envelope placed in the abdominal cavity of the animal or human patient following a surgical procedure.

Further Embodiments

In some embodiments, an article is included herein that has a conformable backing member and a pressure-sensitive adhesive (PSA). The PSA can include a poly(D,L-lactide-co-glycolide-co-ε-caprolactone) having a molecular weight ($M_w$) of 140,000 Daltons or less and a polydispersity index (PDI) of less than 2.0; wherein the poly(D,L-lactide-co-glycolide-co-ε-caprolactone) exhibits storage modulus (G') values of from about $1.5 \times 10^5$ Pa to about $5.5 \times 10^5$ Pa, over a frequency of from about 0.1 to about 1 Hz; and exhibits storage modulus (G') values of from about $1.0 \times 10^6$ Pa to about $4.0 \times 10^6$ Pa, over a frequency of from about $10^2$ to about $10^4$ Hz at 30° C., and having a surface of the PSA coated to the conformable backing member. The PSA can coat 0.1% to 100% of the surface area of the conformable backing member.

In some embodiments, the PSA of the article further includes a bioactive agent. A release liner can be included having a surface thereof adhered to the adhesive surface of the pressure-sensitive adhesive. In an embodiment the conformable backing member further comprises a bioactive layer. In some embodiments the article is a wound dressing. In some embodiments the PSA comprises an enzyme inhibitor to increase wound healing. In some embodiments the conformable backing member comprises gauze. In some embodiments the PSA comprises impregnation with chlorhexidine gluconate. In some embodiments the article is an anti-microbial carrier. In some embodiments the article is used to treat decubitis ulcers. In some embodiments the article is wrapped around an internal tissue or bone. In some embodiments the internal tissue is a resectioned bowel. In some embodiments the article is wrapped around a bone comprising a fracture, break, or is in need of medical treatment. In some embodiments the article is formed into a sealable package. In some embodiments the article formed is an envelope. In some embodiments the article formed contains a gel or liquid comprising a bioactive agent. In some embodiments the article is a diaper. In some embodiments the edges or seams of the diaper are adhered with the PSA. In some embodiments the article is compostable packing. In some embodiments the edges or seams of the compostable packing are adhered with the PSA. In some embodiments the poly(D,L-lactide-co-glycolide-co-ε-caprolactone) comprises from 10 to 60 mol % D,L-lactide, from 10 to 50 mol % D,L-glycolide, and from 10 to 80 mol % ε-caprolactone. In some embodiments the poly(D,L-lactide-co-glycolide-co-ε-caprolactone) comprises from 20 to 40 mol % D,L-lactide, from 10 to 30 mol % D,L-glycolide, and from 40 to 60 mol % ε-caprolactone. In some embodiments the poly(D,L-lactide-co-glycolide-co-ε-caprolactone) comprises 30 mol % D,L-lactide, 20 mol % D,L-glycolide, and 50 mol % ε-caprolactone. In some embodiments the poly(D,L-lactide-co-glycolide-co-ε-caprolactone) has a molecular weight ($M_w$) of from 60,000 to 130,000 Daltons. In some embodiments the poly(D,L-lactide-co-glycolide-co-ε-caprolactone) has a polydispersity index (PDI) ranging from 1.5 to 1.8.

In some embodiments, an article is included herein that has a conformable backing member and a pressure-sensitive adhesive (PSA). The PSA can include a blend including (a) a first poly(D,L-lactide-co-glycolide-co-ε-caprolactone) having a molecular weight ($M_w$) of from 75,000 to 250,000 Daltons and a polydispersity index (PDI) of less than 2.0, and (b) a second poly(D,L-lactide-co-glycolide-co-ε-caprolactone) having a molecular weight ($M_w$) of 130,000 Daltons or less and a polydispersity index (PDI) of less than 2.0. The second poly(D,L-lactide-co-glycolide-co-ε-caprolactone)

can have a molecular weight ($M_w$) that is less than the first poly(D,L-lactide-co-glycolide-co-ε-caprolactone). The weight ratio of the first poly(D,L-lactide-co-glycolide-co-ε-caprolactone) to the second poly(D,L-lactide-co-glycolide-co-ε-caprolactone) can be from about 90:10 to about 60:40. A surface of the PSA can be coated to the conformable backing member. The PSA can coat from 0.1% to 100% of the surface area of the conformable backing member.

In some embodiments, the PSA of the article further includes a bioactive agent. A release liner can be included having a surface thereof adhered to the adhesive surface of the pressure-sensitive adhesive. In an embodiment the conformable backing member further comprises a bioactive layer. In some embodiments the article is a wound dressing. In some embodiments the PSA comprises an enzyme inhibitor to increase wound healing. In some embodiments the conformable backing member comprises gauze. In some embodiments the PSA comprises impregnation with chlorhexidine gluconate. In some embodiments the article is an anti-microbial carrier. In some embodiments the article is used to treat decubitis ulcers. In some embodiments the article is wrapped around an internal tissue or bone. In some embodiments the internal tissue is a resectioned bowel. In some embodiments the article is wrapped around a bone comprising a fracture, break, or is in need of medical treatment. In some embodiments the article is formed into a sealable package. In some embodiments the article formed is an envelope. In some embodiments the article formed contains a gel or liquid comprising a bioactive agent. In some embodiments the article is a diaper. In some embodiments the edges or seams of the diaper are adhered with the PSA. In some embodiments the article is compostable packing. In some embodiments the edges or seams of the compostable packing are adhered with the PSA. In some embodiments, the weight ratio of the first poly(D,L-lactide-co-glycolide-co-ε-caprolactone) to the second poly(D,L-lactide-co-glycolide-co-ε-caprolactone) is from about 85:15 to about 70:30. In some embodiments, the first poly(D,L-lactide-co-glycolide-co-ε-caprolactone) has a molecular weight ($M_w$) of from 100,000 to 130,000 Daltons. In some embodiments, the second poly(D,L-lactide-co-glycolide-co-ε-caprolactone) has a molecular weight ($M_w$) of from 60,000 to 130,000 Daltons. In some embodiments, the first poly(D,L-lactide-co-glycolide-co-ε-caprolactone) has a polydispersity index (PDI) ranging from 1.5 to 1.8.

In some embodiments, an article is included herein that has a conformable backing member and a pressure-sensitive adhesive (PSA). The PSA can be a blend including (a) a poly(D,L-lactide-co-glycolide-co-ε-caprolactone) having a molecular weight of from 75,000 to 250,000 Daltons and a polydispersity index (PDI) of less than 2.0, and (b) a poly(D,L-lactide-co-glycolide-co-mPEG) having a molecular weight of less than 25,000 Daltons and a polydispersity index (PDI) of less than 2.0. The weight ratio of the poly(D,L-lactide-co-glycolide-co-ε-caprolactone) to the poly(D,L-lactide-co-glycolide-co-mPEG) can be from about 95:5 to about 75:25. A surface of the PSA can be coated to the conformable backing member. The PSA can coat 0.1% to 100% of the surface area of the conformable backing member.

In some embodiments, the PSA of the article further includes a bioactive agent. A release liner can be included having a surface thereof adhered to the adhesive surface of the pressure-sensitive adhesive. In an embodiment the conformable backing member further comprises a bioactive layer. In some embodiments the article is a wound dressing. In some embodiments the PSA comprises an enzyme inhibitor to increase wound healing. In some embodiments the conformable backing member comprises gauze. In some embodiments the PSA comprises impregnation with chlorhexidine gluconate. In some embodiments the article is an anti-microbial carrier. In some embodiments the article is used to treat decubitis ulcers. In some embodiments the article is wrapped around an internal tissue or bone. In some embodiments the internal tissue is a resectioned bowel. In some embodiments the article is wrapped around a bone comprising a fracture, break, or is in need of medical treatment. In some embodiments the article is formed into a sealable package. In some embodiments the article formed is an envelope. In some embodiments the article formed contains a gel or liquid comprising a bioactive agent. In some embodiments the article is a diaper. In some embodiments the edges or seams of the diaper are adhered with the PSA. In some embodiments the article is compostable packing. In some embodiments the edges or seams of the compostable packing are adhered with the PSA. In some embodiments the article of claim 50, wherein the weight ratio of the poly(D,L-lactide-co-glycolide-co-ε-caprolactone) to the poly(D,L-lactide-co-glycolide-co-mPEG) is from about 90:10 to about 85:15. In some embodiments the article of claim 50, wherein the poly(D,L-lactide-co-glycolide-co-ε-caprolactone) has a molecular weight ($M_w$) of from 100,000 to 130,000 Daltons. In some embodiments the poly(D,L-lactide-co-glycolide-co-mPEG) has a molecular weight ($M_w$) of from 10,000 to 20,000 Daltons. In some embodiments the poly(D,L-lactide-co-glycolide-co-ε-caprolactone) has a polydispersity index (PDI) ranging from 1.5 to 1.8. In some embodiments the poly(D,L-lactide-co-glycolide-co-mPEG) has a polydispersity index (PDI) ranging from 1.4 to 1.7.

What is claimed is:

1. An article comprising:
   a conformable backing member comprising a sheet; and
   a pressure-sensitive adhesive (PSA) comprising a poly(D,L-lactide-co-glycolide-co-ε-caprolactone) having a molecular weight ($M_w$) of from 60,000 to 130,000 Daltons and a polydispersity index (PDI) of less than 2.0; wherein the poly(D,L-lactide-co-glycolide-co-ε-caprolactone) exhibits storage modulus (G') values of from about $1.5 \times 10^5$ Pa to about $5.5 \times 10^5$ Pa, over a frequency of from about 0.1 to about 1 Hz; and exhibits storage modulus (G') values of from about $1.0 \times 10^6$ Pa to about $4.0 \times 10^6$ Pa, over a frequency of from about $10^2$ to about $10^4$ Hz at 30° C., and having a surface thereof coated to the conformable backing member;
   wherein the PSA coats 0.1% to 100% of the surface area of the conformable backing member.

2. The article of claim 1, wherein the PSA further comprises a bioactive agent.

3. The article of claim 1, wherein the conformable backing member further comprises a bioactive layer.

4. The article of claim 1, wherein the PSA comprises an enzyme inhibitor to increase wound healing.

5. The article of claim 1, wherein the conformable backing member comprises gauze.

6. The article of claim 1, wherein the PSA is impregnated with chlorhexidine gluconate.

7. The article of claim 1, wherein the article is an anti-microbial carrier.

8. The article of claim 1, wherein the article is wrapped around an internal tissue or bone.

9. The article of claim 1, wherein the article is formed into a sealable package.

10. The article of claim 9, wherein the article formed is an envelope.

11. The article of claim 9, wherein the article formed contains a gel or liquid comprising a bioactive agent.

12. The article of claim 1, wherein the article is a diaper and the edges or seams of the diaper are adhered with the PSA.

13. The article of claim 1, wherein the article is compostable packing and the edges or seams of the compostable packing are adhered with the PSA.

14. The article of claim 1, wherein the poly(D,L-lactide-co-glycolide-co-ϵ-caprolactone) comprises from 10 to 60 mol % D,L-lactide, from 10 to 50 mol % D,L-glycolide, and from 10 to 80 mol % ϵ-caprolactone.

15. The article of claim 1, wherein the poly(D,L-lactide-co-glycolide-co-ϵ-caprolactone) comprises from 20 to 40 mol % D,L-lactide, from 10 to 30 mol % D,L-glycolide, and from 40 to 60 mol % ϵ-caprolactone.

16. The article of claim 1, wherein the poly(D,L-lactide-co-glycolide-co-ϵ-caprolactone) comprises 30 mol % D,L-lactide, 20 mol % D,L-glycolide, and 50 mol % ϵ-caprolactone.

17. The article of claim 1, wherein the poly(D,L-lactide-co-glycolide-co-ϵ-caprolactone) has a polydispersity index (PDI) ranging from 1.5 to 1.8.

18. The article of claim 1, wherein the poly(D,L-lactide-co-glycolide-co-ϵ-caprolactone) has a molecular weight ($M_w$) of from 100,000 to 130,000 Daltons.

19. An article, comprising:
a conformable backing member comprising a sheet; and
a pressure-sensitive adhesive (PSA) comprising a blend comprising:
(a) a first poly(D,L-lactide-co-glycolide-co-ϵ-caprolactone) having a molecular weight ($M_w$) of from 75,000 to 250,000 Daltons and a polydispersity index (PDI) of less than 2.0, and
(b) a second poly(D,L-lactide-co-glycolide-co-ϵ-caprolactone) having a molecular weight ($M_w$) of 130,000 Daltons or less and a polydispersity index (PDI) of less than 2.0;
wherein the second poly(D,L-lactide-co-glycolide-co-ϵ-caprolactone) has a molecular weight ($M_w$) that is less than the first poly(D,L-lactide-co-glycolide-co-ϵ-caprolactone); and
wherein the weight ratio of the first poly(D,L-lactide-co-glycolide-co-ϵ-caprolactone) to the second poly(D,L-lactide-co-glycolide-co-ϵ-caprolactone) is from about 90:10 to about 60:40,
and having a surface of the PSA coated to the conformable backing member;
wherein the PSA coats 0.1% to 100% of the surface area of the conformable backing member.

20. An article, comprising:
a conformable backing member comprising a sheet; and
a pressure-sensitive adhesive (PSA) comprising a blend comprising
(a) a poly(D,L-lactide-co-glycolide-co-ϵ-caprolactone) having a molecular weight of from 75,000 to 250,000 Daltons and a polydispersity index (PDI) of less than 2.0, and
(b) a poly(D,L-lactide-co-glycolide-co-mPEG) having a molecular weight of less than 25,000 Daltons and a polydispersity index (PDI) of less than 2.0; and
wherein the weight ratio of the poly(D,L-lactide-co-glycolide-co-ϵ-caprolactone) to the poly(D,L-lactide-co-glycolide-co-mPEG) is from about 95:5 to about 75:25,
and having a surface of the PSA coated to the conformable backing member;
wherein the PSA coats 0.1% to 100% of the surface area of the conformable backing member.

* * * * *